United States Patent [19]

Edwards et al.

[11] Patent Number: 5,736,363
[45] Date of Patent: Apr. 7, 1998

[54] IGF-II ANALOGUES

[75] Inventors: Richard Mark Edwards; Lindsay Bawden, both of Oxford, England

[73] Assignee: British Bio-technology Limited, England

[21] Appl. No.: 190,029

[22] PCT Filed: Jul. 27, 1992

[86] PCT No.: PCT/GB92/01389

§ 371 Date: Feb. 28, 1994

§ 102(e) Date: Feb. 28, 1994

[87] PCT Pub. No.: WO93/03152

PCT Pub. Date: Feb. 18, 1993

[30] Foreign Application Priority Data

Jul. 29, 1991 [GB] United Kingdom .................. 9116325
Feb. 5, 1992 [GB] United Kingdom .................. 9202401

[51] Int. Cl.$^6$ .............. C12P 21/06; A61K 38/30; C07L 14/65
[52] U.S. Cl. .................. 435/69.4; 514/2; 530/303; 530/399
[58] Field of Search ................... 530/399, 303; 435/69.4, 69.1

[56] References Cited

U.S. PATENT DOCUMENTS 4,451,396 5/1984 DiMarchi .......................... 260/112

FOREIGN PATENT DOCUMENTS

| 0 128 733 | 9/1984 | European Pat. Off. . |
| 0 135 094 A1 | 3/1985 | European Pat. Off. . |
| 0 193 112 | 9/1986 | European Pat. Off. . |
| 0 196 056 A2 | 10/1986 | European Pat. Off. . |
| 0 224 885 A1 | 6/1987 | European Pat. Off. . |
| 0 230 869 A2 | 8/1987 | European Pat. Off. . |
| 0 280 460 A2 | 8/1988 | European Pat. Off. . |
| 0 289 314 A3 | 11/1988 | European Pat. Off. . |
| 0 361 956 A2 | 4/1990 | European Pat. Off. . |
| 2 163751 | 3/1986 | United Kingdom . |
| WO 86/00619 | 1/1986 | WIPO . |
| WO 89/03423 | 4/1989 | WIPO . |
| WO 89/03424 | 4/1989 | WIPO . |
| WO 89/05822 | 6/1989 | WIPO . |
| WO 89/15142 | 12/1990 | WIPO . |

OTHER PUBLICATIONS

Li et al 1983 P.N.A.S. 80:2216–2220.
Tong et al. (1988), *J. Biol. Chem.*, vol. 263, pp. 2585–2588.
Daughaday et al. (1988), *New Eng. J. Med.*, vol. 319, 1434–1440.
Baxter, R.C. (1988), *Comp. Biochem. Physiol.*, vol. 91B, pp. 229–235.
Shuster et al. (1989), *Gene*, vol. 83, pp. 47–55.
Moks et al. (1987), *Bio/Technology*, vol. 5, pp. 379–382.
Hard et al. (1989), *FEBS Letter*, vol. 248, pp. 111–114.
Forsberg et al. (1990), *Biochem. J.*, vol. 271, pp. 357–363.
Hammerberg et al. (1989), *Proc. Natl. Acad. Sci. USA*, vol. 86, pp. 4367–4371.
Furman et al. (1987), *Bio/Technology*, vol. 5, pp. 1047–1051.
McBrice et al. (1983), *Tetrahedron Letters*, vol. 24, p. 245.
Biggin et al. (1983), *Proc. Natl. Acad. Sci. USA*, vol. 80, pp. 3963–3965.
Dafgard et al. (1985), *J. Cell Science*, Suppl. 3, pp. 53–64.
Rinderknecht and Humbel (1978), *FEBS Letters*, vol. 89(2), pp. 283–286.
Smith et al. (1990), *J. Biol. Chem.*, vol. 265(22), pp. 13335–13343.

*Primary Examiner*—Vasu S. Jagannathan
*Assistant Examiner*—K. Cochrane Carlson
*Attorney, Agent, or Firm*—Banner & Witcoff, Ltd.

[57] ABSTRACT

Insulin-like Growth Factor II (IGF-II) analogues in which at least one of R37 and R38 is replaced with another amino acid residue, the most preferred being IGF-II R37Q R38Q, can readily be produced in *E. coli*, unlike natural IGF-II, which is cleaved on secretion. The analogues retain activity on the type I and type II IGF receptors but have lower affinity for the insulin receptor; they are therefore more specific in their action.

9 Claims, 12 Drawing Sheets

FIG. 3

```
      M   A   Y   R   P   S   E   T   L   C   G   G   E   L   V   D   T
GCATGCATATGGCATACCGCCCGAGCGAGACCCTGTGCGGTGGCGAGCTCGTAGACACTC
SphI NdeI                                     SacI
         10         20         30         40         50         60

L   Q   F   V   C   G   D   R   G   F   Y   F   S   R   P   A   S   R   V   S
CGTACGTATACCGTATGGCGGGCTTTGTGGTGACCGTGGCTTCTACTTCTCTCGTCCTGCTAGCCGTGTATCTC
         PstI       BstEII                              NheI
         70         80         90        100        110        120

R   R   S   R   G   I   V   E   E   C   C   F   R   S   C   D   L   A   L   L
ACGTCAAGCAAACACCACTGGCACCGTGGAAGAGTGCTGTTTCCGCAGCTGTGATCTGGCACTGCTCG
                        XbaI                         PvuII
        130        140        150        160        170        180

E   T   Y   C   A   T   P   A   K   S   E   *
CGGCCAAGATCTTCCGTAGCAACTTCTCACGACAAAGGCGTTGACCGTGACGAGC

AAACTTACTGCGCAACTCCAGCAAATCCGAATAAGGATCC
     FspI                              BamHI
TTTGAATGACGCGTTCAGGTCGTTTTAGGCTTATTCCTAGG
        190        200        210        220
```

FIG. 5A

```
P   A   S   R   V   S     R   R   S   R   G   I   V   E   E   C   C
TCCTGCTAGCCGTGTATCTCGCCGTTCTAGAGGCATCGTTGAAGAGTGCTGT
||||||||||||||||||||*****|||||||||||||||||||||||||||
         3' gcacatagagtcgttagatctcc 5' BB1551
       110           120            130           140           150

|
                    primer extension
                       ligation
                      transfection
                       sequencing
                            |
                            V P   A   S   R   V   S   Q   Q   S   R   G   I   V   E   E   C   C
TCCTGCTAGCCGTGTATCTCAGCAATCTAGAGGCATCGTTGAAGAGTGCTGT
|||||||||||||||||||||||||||||||||||||||||||||||||||
AGGACGATCGgcacatagagtcgttagatctccGTAGCAACTTCTCACGACA
       110           120           130           140           150
```

FIG. 5B

```
  P   A   S   R   V   S   R   R   S   R   G   I   V   E   E   C   C
TCCTGCTAGCCCGTGTATCTCGCCCGTTCTAGAGGCATCGTTGAAGAGTGCTGT
||||||||||||||||||||||||*****|||||
       3' GCACATAGANNNNNNAGATCTCCG 5'  BB1550
          110         120         130         140         150
```

```
        |
  primer extension
  ligation
  transfection
  sequencing
        |
        V
```

```
  P   A   S   R   V   S   ?   ?   S   R   G   I   V   E   E   C   C
TCCTGCTAGCCCGTGTATCTNNNNNNTCTAGAGGCATCGTTGAAGAGTGCTGT
|||||||||||||||||||||||||||||||||||||||||||||||||||
AGGACGATCGgcacatagannnnnnagatctCCGTAGCAACTTCTCACGACA
          110         120         130         140         150
```

PSD 15 ⟶  53 54 55 56 57  ⟵ PSD 15

PSD 15 ⟶  58 59 60 61 62  ⟵ PSD 15

|  | L→R |  | Kda p.s.m |
|---|---|---|---|
| Lane 1 | – | pre-stained markers | 43.0 |
| Lane 2 | – | pre-cleaved material | 29.0 |
| Lane 3 | – | cleaved material | 18.4 |
| Lane 4 | – | post mono Q | 14.3 |
| Lane 5 | – | post HPLC (JLP) | 6.2 |
| Lane 6 | – | p.s.m. | 2.3 |

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
        (A) LENGTH: 67 amino acids
        (B) TYPE: amino acid
        (D) TOPOLOGY: linear (ii) MOLECULE TYPE: protein (vi) ORIGINAL SOURCE:
        (A) ORGANISM: Homo sapiens (ix) FEATURE:
        (A) NAME/KEY: Cleavage-site
        (B) LOCATION: 37..38

(xi) SEQUENCE DESCRIPTION: SEQ ID NO:1:

```
Ala Tyr Arg Pro Ser Glu Thr Leu Cys Gly Gly Glu Leu Val Asp Thr
 1               5                  10                  15
Leu Gln Phe Val Cys Gly Asp Arg Gly Phe Tyr Phe Ser Arg Pro Ala
                20                  25                  30
Ser Arg Val Ser Arg Arg Ser Arg Gly Ile Val Glu Glu Cys Cys Phe
                35                  40                  45
Arg Ser Cys Asp Leu Ala Leu Leu Glu Thr Tyr Cys Ala Thr Pro Ala
        50                  55                  60
Lys Ser Glu
        65
```

(2) INFORMATION FOR SEQ ID NO:2:

(i) SEQUENCE CHARACTERISTICS:
        (A) LENGTH: 67 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: HOMO SAPIENS (ix) FEATURE:
        (A) NAME/KEY: Modified-site
        (B) LOCATION: 37..38
        (D) OTHER INFORMATION: /note= "Protease resistant mutant form of IGF- II with Arg-37 modified to Gln and Arg-38 modified to Gln. Resistance to cleavage by the E. coli periplasmic protease and reduced affinity for the insulin receptor (xi) SEQUENCE DESCRIPTION: SEQ ID NO:2:

```
Ala Tyr Arg Pro Ser Glu Thr Leu Cys Gly Gly Glu Leu Val Asp Thr
 1               5                  10                  15
Leu Gln Phe Val Cys Gly Asp Arg Gly Phe Tyr Phe Ser Arg Pro Ala
                20                  25                  30
Ser Arg Val Ser Gln Gln Ser Arg Gly Ile Val Glu Glu Cys Cys Phe
                35                  40                  45
```

```
          Arg  Ser  Cys  Asp  Leu  Ala  Leu  Leu  Glu  Thr  Tyr  Cys  Ala  Thr  Pro  Ala
               50                  55                       60

Lys  Ser  Glu
          65
```

( 2 ) INFORMATION FOR SEQ ID NO:3:

( i ) SEQUENCE CHARACTERISTICS:
    ( A ) LENGTH: 221 base pairs
    ( B ) TYPE: nucleic acid
    ( C ) STRANDEDNESS: double
    ( D ) TOPOLOGY: linear ( i i ) MOLECULE TYPE: DNA (genomic)

( v i ) ORIGINAL SOURCE:
    ( A ) ORGANISM: Homo sapiens ( i x ) FEATURE:
    ( A ) NAME/KEY: CDS
    ( B ) LOCATION: 9..212
    ( D ) OTHER INFORMATION: /codon_start= 9
      / function= "Synthetic gene for mature human
      IGF-ii"
      / product= "Synthetic DNA"

( i x ) FEATURE:
    ( A ) NAME/KEY: misc_feature
    ( B ) LOCATION: 1..6
    ( D ) OTHER INFORMATION: /function="SphI site"
      / number= 1

( i x ) FEATURE:
    ( A ) NAME/KEY: misc_feature
    ( B ) LOCATION: 6..12
    ( D ) OTHER INFORMATION: /function="NdeI site"
      / number= 2

( i x ) FEATURE:
    ( A ) NAME/KEY: misc_feature
    ( B ) LOCATION: 216..221
    ( D ) OTHER INFORMATION: /function="BamHI cleavage site"

( x i ) SEQUENCE DESCRIPTION: SEQ ID NO:3:

```
GCATGCAT ATG  GCA  TAC  CGC  CCG  AGC  GAG  ACC  CTG  TGC  GGT  GGC  GAG  CTC         50
         Met  Ala  Tyr  Arg  Pro  Ser  Glu  Thr  Leu  Cys  Gly  Gly  Glu  Leu
         1                  5                            10

GTA  GAC  ACT  CTG  CAG  TTC  GTT  TGT  GGT  GAC  CGT  GGC  TTC  TAC  TTC  TCT        98
Val  Asp  Thr  Leu  Gln  Phe  Val  Cys  Gly  Asp  Arg  Gly  Phe  Tyr  Phe  Ser
15                      20                      25                      30

CGT  CCT  GCT  AGC  CGT  GTA  TCT  CGC  CGT  TCT  AGA  GGC  ATC  GTT  GAA  GAG       146
Arg  Pro  Ala  Ser  Arg  Val  Ser  Arg  Arg  Ser  Arg  Gly  Ile  Val  Glu  Glu
                    35                       40                      45

TGC  TGT  TTC  CGC  AGC  TGT  GAT  CTG  GCA  CTG  CTC  GAA  ACT  TAC  TGC  GCA       194
Cys  Cys  Phe  Arg  Ser  Cys  Asp  Leu  Ala  Leu  Leu  Glu  Thr  Tyr  Cys  Ala
               50                       55                      60

ACT  CCA  GCA  AAA  TCC  GAA  TAAGGATCC                                              221
Thr  Pro  Ala  Lys  Ser  Glu
               65
```

( 2 ) INFORMATION FOR SEQ ID NO:4:

( i ) SEQUENCE CHARACTERISTICS:
    ( A ) LENGTH: 68 amino acids
    ( B ) TYPE: amino acid
    ( D ) TOPOLOGY: linear ( i i ) MOLECULE TYPE: protein ( x i ) SEQUENCE DESCRIPTION: SEQ ID NO:4:

```
Met  Ala  Tyr  Arg  Pro  Ser  Glu  Thr  Leu  Cys  Gly  Gly  Glu  Leu  Val  Asp
```

```
                    1                   5                        10                        15
```

Thr Leu Gln Phe Val Cys Gly Asp Arg Gly Phe Tyr Phe Ser Arg Pro
                    20                      25                        30

Ala Ser Arg Val Ser Arg Arg Ser Arg Gly Ile Val Glu Glu Cys Cys
            35                      40                  45

Phe Arg Ser Cys Asp Leu Ala Leu Leu Glu Thr Tyr Cys Ala Thr Pro
        50                      55                  60

Ala Lys Ser Glu
65

( 2 ) INFORMATION FOR SEQ ID NO:5:

( i ) SEQUENCE CHARACTERISTICS:
        ( A ) LENGTH: 102 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Homo sapiens ( i x ) FEATURE:
        ( A ) NAME/KEY: CDS
        ( B ) LOCATION: 2..102
        ( D ) OTHER INFORMATION: /codon_start= 2
            / function= "Synthetic ompA leader sequence"
            / product= "Synthetic DNA"

( i x ) FEATURE:
        ( A ) NAME/KEY: misc_feature
        ( B ) LOCATION: 1..6
        ( D ) OTHER INFORMATION: /function="NdeI cleavage site"

( i x ) FEATURE:
        ( A ) NAME/KEY: misc_feature
        ( B ) LOCATION: 100..102
        ( D ) OTHER INFORMATION: /function="SacI cleavage site"

( i x ) FEATURE:
        ( A ) NAME/KEY: misc_feature
        ( B ) LOCATION: 2..65
        ( D ) OTHER INFORMATION: /function="ompA leader sequence"

( i x ) FEATURE:
        ( A ) NAME/KEY: misc_feature
        ( B ) LOCATION: 66..102
        ( D ) OTHER INFORMATION: /function="IGF-II gene (part)"

( x i ) SEQUENCE DESCRIPTION: SEQ ID NO:5:

```
T ATG AAA AAG ACA GCT ATC GCG ATT GCA GTG GCA CTG GCT GGT TTC         46
  Met Lys Lys Thr Ala Ile Ala Ile Ala Val Ala Leu Ala Gly Phe
  1               5                   10                  15

GCG ACC GTA GCG CAG GCC GCA TAC CGC CCG AGC GAG ACC CTG TGC GGT       94
Ala Thr Val Ala Gln Ala Ala Tyr Arg Pro Ser Glu Thr Leu Cys Gly
             20                  25                  30

GGC GAG CT                                                           102
Gly Glu Leu
```

( 2 ) INFORMATION FOR SEQ ID NO:6:

( i ) SEQUENCE CHARACTERISTICS:
        ( A ) LENGTH: 34 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

-continued

```
Met Lys Lys Thr Ala Ile Ala Ile Ala Val Ala Leu Ala Gly Phe Ala
 1            5                   10                  15
Thr Val Ala Gln Ala Ala Tyr Arg Pro Ser Glu Thr Leu Cys Gly Gly
            20                  25                  30
Glu Leu
```

( 2 ) INFORMATION FOR SEQ ID NO:7:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( i x ) FEATURE:
        ( A ) NAME/KEY: misc_feature
        ( B ) LOCATION: 1..23
        ( D ) OTHER INFORMATION: /function="directs substitution of
            Gln for Arg at positions 37 and 38"
            / product= "IGF-II mutagenesis primer"

( x i ) SEQUENCE DESCRIPTION: SEQ ID NO:7:

CCTCTAGATT GCTGAGATAC ACG                                23

( 2 ) INFORMATION FOR SEQ ID NO:8:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( i x ) FEATURE:
        ( A ) NAME/KEY: misc_feature
        ( B ) LOCATION: 1..24
        ( D ) OTHER INFORMATION: /function="directs random
            substitution at Arg-37 and Arg-38"
            / product= "IGF-II mutagenesis primer"

( x i ) SEQUENCE DESCRIPTION: SEQ ID NO:8:

GCCTCTAGAN NNNNNAGATA CACG                             24

( 2 ) INFORMATION FOR SEQ ID NO:9:

( i ) SEQUENCE CHARACTERISTICS:
        ( A ) LENGTH: 1072 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Homo sapiens ( i x ) FEATURE:
        ( A ) NAME/KEY: CDS
        ( B ) LOCATION: 11..1057
        ( D ) OTHER INFORMATION: /codon_start= 11
            / function= "Gene for IGF-II/HRP fusion protein"
            / product= "Synthetic DNA"

( i x ) FEATURE:

(A) NAME/KEY: misc_feature
(B) LOCATION: 1..6
(D) OTHER INFORMATION: /function="HinDIII cleavage site"

(ix) FEATURE:
(A) NAME/KEY: misc_feature
(B) LOCATION: 1067..1072
(D) OTHER INFORMATION: /function="EcoRI cleavage site"

(ix) FEATURE:
(A) NAME/KEY: misc_feature
(B) LOCATION: 11..856
(D) OTHER INFORMATION: /function="HRP coding sequence
(fragment)"

(ix) FEATURE:
(A) NAME/KEY: misc_feature
(B) LOCATION: 857..1057
(D) OTHER INFORMATION: /function="IGF-II coding sequence"

(xi) SEQUENCE DESCRIPTION: SEQ ID NO:9:

```
AAGCTTAACC ATG CAG TTA ACC CCT ACA TTC TAC GAC AAT AGC TGT CCC         49
           Met Gln Leu Thr Pro Thr Phe Tyr Asp Asn Ser Cys Pro
           1               5                   10

AAC GTG TCC AAC ATC GTT CGC GAC ACA ATC GTC AAC GAG CTC AGA TCC        97
Asn Val Ser Asn Ile Val Arg Asp Thr Ile Val Asn Glu Leu Arg Ser
15                  20                  25

GAT CCC AGG ATC GCT GCT TCA ATA TTA CGT CTG CAC TTC CAT GAC TGC       145
Asp Pro Arg Ile Ala Ala Ser Ile Leu Arg Leu His Phe His Asp Cys
30                  35                  40                  45

TTC GTG AAT GGT TGC GAC GCT AGC ATA TTA CTG GAC AAC ACC ACC AGT       193
Phe Val Asn Gly Cys Asp Ala Ser Ile Leu Leu Asp Asn Thr Thr Ser
            50                  55                  60

TTC CGC ACT GAA AAG GAT GCA TTC GGG AAC GCT AAC AGC GCC AGG GGC       241
Phe Arg Thr Glu Lys Asp Ala Phe Gly Asn Ala Asn Ser Ala Arg Gly
            65                  70                  75

TTT CCA GTG ATC GAT CGC ATG AAG GCT GCC GTT GAG TCA GCA TGC CCA       289
Phe Pro Val Ile Asp Arg Met Lys Ala Ala Val Glu Ser Ala Cys Pro
        80                  85                  90

CGA ACA GTC AGT TGT GCA GAC CTG CTG ACT ATA GCT GCG CAA CAG AGC       337
Arg Thr Val Ser Cys Ala Asp Leu Leu Thr Ile Ala Ala Gln Gln Ser
95                  100                 105

GTG ACT CTT GCA GGC GGA CCG TCC TGG AGA GTG CCG CTC GGT CGA CGT       385
Val Thr Leu Ala Gly Gly Pro Ser Trp Arg Val Pro Leu Gly Arg Arg
110                 115                 120                 125

GAC TCC CTA CAG GCA TTC CTA GAT CTG GCC AAC GCC AAC TTG CCT GCT       433
Asp Ser Leu Gln Ala Phe Leu Asp Leu Ala Asn Ala Asn Leu Pro Ala
                130                 135                 140

CCA TTC TTC ACC CTG CCC CAG CTG AAG GAT AGC TTT AGA AAC GTG GGT       481
Pro Phe Phe Thr Leu Pro Gln Leu Lys Asp Ser Phe Arg Asn Val Gly
            145                 150                 155

CTG AAT CGC TCG AGT GAC CTT GTG GCT CTG TCC GGA GGA CAC ACA TTT       529
Leu Asn Arg Ser Ser Asp Leu Val Ala Leu Ser Gly Gly His Thr Phe
        160                 165                 170

GGA AAG AAC CAG TGT AGG TTC ATC ATG GAT AGG CTC TAC AAT TTC AGC       577
Gly Lys Asn Gln Cys Arg Phe Ile Met Asp Arg Leu Tyr Asn Phe Ser
175                 180                 185

AAC ACT GGG TTA CCT GAC CCC ACG CTG AAC ACT ACG TAT CTC CAG ACA       625
Asn Thr Gly Leu Pro Asp Pro Thr Leu Asn Thr Thr Tyr Leu Gln Thr
190                 195                 200                 205

CTG AGA GGC TTG TGC CCA CTG AAT GGC AAC CTC AGT GCA CTA GTG GAC       673
Leu Arg Gly Leu Cys Pro Leu Asn Gly Asn Leu Ser Ala Leu Val Asp
            210                 215                 220

TTT GAT CTG CGG ACC CCA ACC ATC TTC GAT AAC AAG TAC TAT GTG AAT       721
Phe Asp Leu Arg Thr Pro Thr Ile Phe Asp Asn Lys Tyr Tyr Val Asn
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 225 |     |     |     |     |     | 230 |     |     |     |     |     | 235 |     |      |
| CTA | GAG | GAG | CAG | AAA | GGC | CTG | ATA | CAG | AGT | GAT | CAA | GAA | CTG | TTT | AGC | 769  |
| Leu | Glu | Glu | Gln | Lys | Gly | Leu | Ile | Gln | Ser | Asp | Gln | Glu | Leu | Phe | Ser |      |
|     |     | 240 |     |     |     |     | 245 |     |     |     |     | 250 |     |     |     |      |
| AGT | CCA | AAC | GCC | ACT | GAC | ACC | ATC | CCA | CTG | GTG | AGA | AGT | TTT | GCT | AAC | 817  |
| Ser | Pro | Asn | Ala | Thr | Asp | Thr | Ile | Pro | Leu | Val | Arg | Ser | Phe | Ala | Asn |      |
|     |     | 255 |     |     |     |     | 260 |     |     |     |     | 265 |     |     |     |      |
| TCT | ACT | CAA | ACC | TTC | TTT | AAC | GCC | TTC | GTG | GAA | GCT | ATG | GCA | TAC | CGC | 865  |
| Ser | Thr | Gln | Thr | Phe | Phe | Asn | Ala | Phe | Val | Glu | Ala | Met | Ala | Tyr | Arg |      |
| 270 |     |     |     |     | 275 |     |     |     |     | 280 |     |     |     |     | 285 |      |
| CCG | AGC | GAG | ACC | CTG | TGC | GGT | GGC | GAG | CTC | GTA | GAC | ACT | CTG | CAG | TTC | 913  |
| Pro | Ser | Glu | Thr | Leu | Cys | Gly | Gly | Glu | Leu | Val | Asp | Thr | Leu | Gln | Phe |      |
|     |     |     |     | 290 |     |     |     |     | 295 |     |     |     |     | 300 |     |      |
| GTT | TGT | GGT | GAC | CGT | GGC | TTC | TAC | TTC | TCT | CGT | CCT | GCT | AGC | CGT | GTA | 961  |
| Val | Cys | Gly | Asp | Arg | Gly | Phe | Tyr | Phe | Ser | Arg | Pro | Ala | Ser | Arg | Val |      |
|     |     |     | 305 |     |     |     |     | 310 |     |     |     |     | 315 |     |     |      |
| TCT | CGC | CGT | TCT | AGA | GGC | ATC | GTT | GAA | GAG | TGC | TGT | TTC | CGC | AGC | TGT | 1009 |
| Ser | Arg | Arg | Ser | Arg | Gly | Ile | Val | Glu | Glu | Cys | Cys | Phe | Arg | Ser | Cys |      |
|     |     | 320 |     |     |     |     | 325 |     |     |     |     | 330 |     |     |     |      |
| GAT | CTG | GCA | CTG | CTC | GAA | ACT | TAC | TGC | GCA | ACT | CCA | GCA | AAA | TCC | GAA | 1057 |
| Asp | Leu | Ala | Leu | Leu | Glu | Thr | Tyr | Cys | Ala | Thr | Pro | Ala | Lys | Ser | Glu |      |
| 335 |     |     |     |     | 340 |     |     |     |     | 345 |     |     |     |     |     |      |
| TAAGGATCCG AATTC |  |  |  |  |  |  |  |  |  |  |  |  |  |  |  | 1072 |

( 2 ) INFORMATION FOR SEQ ID NO:10:

( i ) SEQUENCE CHARACTERISTICS:
        ( A ) LENGTH: 349 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

| Met | Gln | Leu | Thr | Pro | Thr | Phe | Tyr | Asp | Asn | Ser | Cys | Pro | Asn | Val | Ser |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Asn | Ile | Val | Arg | Asp | Thr | Ile | Val | Asn | Glu | Leu | Arg | Ser | Asp | Pro | Arg |
|     |     |     | 20  |     |     |     |     | 25  |     |     |     |     | 30  |     |     |
| Ile | Ala | Ala | Ser | Ile | Leu | Arg | Leu | His | Phe | His | Asp | Cys | Phe | Val | Asn |
|     |     |     | 35  |     |     |     | 40  |     |     |     |     | 45  |     |     |     |
| Gly | Cys | Asp | Ala | Ser | Ile | Leu | Leu | Asp | Asn | Thr | Thr | Ser | Phe | Arg | Thr |
|     | 50  |     |     |     |     | 55  |     |     |     |     | 60  |     |     |     |     |
| Glu | Lys | Asp | Ala | Phe | Gly | Asn | Ala | Asn | Ser | Ala | Arg | Gly | Phe | Pro | Val |
| 65  |     |     |     |     | 70  |     |     |     |     | 75  |     |     |     |     | 80  |
| Ile | Asp | Arg | Met | Lys | Ala | Ala | Val | Glu | Ser | Ala | Cys | Pro | Arg | Thr | Val |
|     |     |     |     | 85  |     |     |     |     | 90  |     |     |     |     | 95  |     |
| Ser | Cys | Ala | Asp | Leu | Leu | Thr | Ile | Ala | Ala | Gln | Gln | Ser | Val | Thr | Leu |
|     |     |     |     | 100 |     |     |     |     | 105 |     |     |     |     | 110 |     |
| Ala | Gly | Gly | Pro | Ser | Trp | Arg | Val | Pro | Leu | Gly | Arg | Arg | Asp | Ser | Leu |
|     |     | 115 |     |     |     |     | 120 |     |     |     |     | 125 |     |     |     |
| Gln | Ala | Phe | Leu | Asp | Leu | Ala | Asn | Ala | Asn | Leu | Pro | Ala | Pro | Phe | Phe |
|     | 130 |     |     |     |     | 135 |     |     |     |     | 140 |     |     |     |     |
| Thr | Leu | Pro | Gln | Leu | Lys | Asp | Ser | Phe | Arg | Asn | Val | Gly | Leu | Asn | Arg |
| 145 |     |     |     |     | 150 |     |     |     |     | 155 |     |     |     |     | 160 |
| Ser | Ser | Asp | Leu | Val | Ala | Leu | Ser | Gly | Gly | His | Thr | Phe | Gly | Lys | Asn |
|     |     |     |     | 165 |     |     |     |     | 170 |     |     |     |     | 175 |     |
| Gln | Cys | Arg | Phe | Ile | Met | Asp | Arg | Leu | Tyr | Asn | Phe | Ser | Asn | Thr | Gly |
|     |     |     | 180 |     |     |     |     | 185 |     |     |     |     | 190 |     |     |

```
Leu  Pro  Asp  Pro  Thr  Leu  Asn  Thr  Thr  Tyr  Leu  Gln  Thr  Leu  Arg  Gly
          195                      200                     205

Leu  Cys  Pro  Leu  Asn  Gly  Asn  Leu  Ser  Ala  Leu  Val  Asp  Phe  Asp  Leu
     210                      215                     220

Arg  Thr  Pro  Thr  Ile  Phe  Asp  Asn  Lys  Tyr  Tyr  Val  Asn  Leu  Glu  Glu
225                      230                     235                          240

Gln  Lys  Gly  Leu  Ile  Gln  Ser  Asp  Gln  Glu  Leu  Phe  Ser  Ser  Pro  Asn
               245                      250                          255

Ala  Thr  Asp  Thr  Ile  Pro  Leu  Val  Arg  Ser  Phe  Ala  Asn  Ser  Thr  Gln
               260                      265                     270

Thr  Phe  Phe  Asn  Ala  Phe  Val  Glu  Ala  Met  Ala  Tyr  Arg  Pro  Ser  Glu
          275                      280                     285

Thr  Leu  Cys  Gly  Gly  Glu  Leu  Val  Asp  Thr  Leu  Gln  Phe  Val  Cys  Gly
     290                      295                     300

Asp  Arg  Gly  Phe  Tyr  Phe  Ser  Arg  Pro  Ala  Ser  Arg  Val  Ser  Arg  Arg
305                      310                     315                          320

Ser  Arg  Gly  Ile  Val  Glu  Glu  Cys  Cys  Phe  Arg  Ser  Cys  Asp  Leu  Ala
               325                      330                          335

Leu  Leu  Glu  Thr  Tyr  Cys  Ala  Thr  Pro  Ala  Lys  Ser  Glu
               340                      345
```

( 2 ) INFORMATION FOR SEQ ID NO:11:

( i ) SEQUENCE CHARACTERISTICS:
        ( A ) LENGTH: 388 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Homo sapiens ( i x ) FEATURE:
        ( A ) NAME/KEY: CDS
        ( B ) LOCATION: 11..373
        ( D ) OTHER INFORMATION: /codon_start= 11
            / function= "Gene for IGF-II/HRP fusion protein"
            / product= "Synthetic DNA"

( i x ) FEATURE:
        ( A ) NAME/KEY: misc_feature
        ( B ) LOCATION: 1..6
        ( D ) OTHER INFORMATION: /function="HindIII cleavage site"

( i x ) FEATURE:
        ( A ) NAME/KEY: misc_feature
        ( B ) LOCATION: 383..388
        ( D ) OTHER INFORMATION: /function="EcoRI cleavage site"

( i x ) FEATURE:
        ( A ) NAME/KEY: misc_feature
        ( B ) LOCATION: 11..172
        ( D ) OTHER INFORMATION: /function="HRP coding sequence"

( i x ) FEATURE:
        ( A ) NAME/KEY: misc_feature
        ( B ) LOCATION: 173..373
        ( D ) OTHER INFORMATION: /function="IGF-II coding sequence"

( x i ) SEQUENCE DESCRIPTION: SEQ ID NO:11:

```
AAGCTTAACC  ATG  CAG  TTA  ACC  CCT  ACA  TTC  TAC  GAC  AAT  AGC  TGT  CCC        49
            Met  Gln  Leu  Thr  Pro  Thr  Phe  Tyr  Asp  Asn  Ser  Cys  Pro
             1             5                          10

AAC  GTG  TCC  AAC  ATC  GTT  CGC  GAC  ACA  ATC  GTC  AAC  GAG  CTC  AGA  TCC    97
Asn  Val  Ser  Asn  Ile  Val  Arg  Asp  Thr  Ile  Val  Asn  Glu  Leu  Arg  Ser
     15                      20                          25
```

| | | | | | | | | | | | | | | | | |
|---|---|---|---|---|---|---|---|---|---|---|---|---|---|---|---|---|
| GAT | CCC | AGG | ATC | GCT | GCT | TCA | ATA | TTA | CGT | CTG | CAC | TTC | CAT | GAC | TGC | 145 |
| Asp | Pro | Arg | Ile | Ala | Ala | Ser | Ile | Leu | Arg | Leu | His | Phe | His | Asp | Cys | |
| 30 | | | | 35 | | | | | 40 | | | | | | 45 | |
| TTC | GTG | AAT | GGT | TGC | GAC | GCT | AGT | ATG | GCA | TAC | CGC | CCG | AGC | GAG | ACC | 193 |
| Phe | Val | Asn | Gly | Cys | Asp | Ala | Ser | Met | Ala | Tyr | Arg | Pro | Ser | Glu | Thr | |
| | | | | 50 | | | | | 55 | | | | | 60 | | |
| CTG | TGC | GGT | GGC | GAG | CTC | GTA | GAC | ACT | CTG | CAG | TTC | GTT | TGT | GGT | GAC | 241 |
| Leu | Cys | Gly | Gly | Glu | Leu | Val | Asp | Thr | Leu | Gln | Phe | Val | Cys | Gly | Asp | |
| | | | 65 | | | | | 70 | | | | | 75 | | | |
| CGT | GGC | TTC | TAC | TTC | TCT | CGT | CCT | GCT | AGC | CGT | GTA | TCT | CGC | CGT | TCT | 289 |
| Arg | Gly | Phe | Tyr | Phe | Ser | Arg | Pro | Ala | Ser | Arg | Val | Ser | Arg | Arg | Ser | |
| | | 80 | | | | | 85 | | | | | 90 | | | | |
| AGA | GGC | ATC | GTT | GAA | GAG | TGC | TGT | TTC | CGC | AGC | TGT | GAT | CTG | GCA | CTG | 337 |
| Arg | Gly | Ile | Val | Glu | Glu | Cys | Cys | Phe | Arg | Ser | Cys | Asp | Leu | Ala | Leu | |
| | 95 | | | | | 100 | | | | 105 | | | | | | |
| CTC | GAA | ACT | TAC | TGC | GCA | ACT | CCA | GCA | AAA | TCC | GAA | TAAGGATCCG | | | | 383 |
| Leu | Glu | Thr | Tyr | Cys | Ala | Thr | Pro | Ala | Lys | Ser | Glu | | | | | |
| 110 | | | | | 115 | | | | | 120 | | | | | | |
| AATTC | | | | | | | | | | | | | | | | 388 |

( 2 ) INFORMATION FOR SEQ ID NO:12:

( i ) SEQUENCE CHARACTERISTICS:
        ( A ) LENGTH: 121 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

| | | | | | | | | | | | | | | |
|---|---|---|---|---|---|---|---|---|---|---|---|---|---|---|
| Met | Gln | Leu | Thr | Pro | Thr | Phe | Tyr | Asp | Asn | Ser | Cys | Pro | Asn | Val | Ser |
| 1 | | | | 5 | | | | | 10 | | | | | 15 | |
| Asn | Ile | Val | Arg | Asp | Thr | Ile | Val | Asn | Glu | Leu | Arg | Ser | Asp | Pro | Arg |
| | | | 20 | | | | | 25 | | | | | 30 | | |
| Ile | Ala | Ala | Ser | Ile | Leu | Arg | Leu | His | Phe | His | Asp | Cys | Phe | Val | Asn |
| | | 35 | | | | | 40 | | | | | 45 | | | |
| Gly | Cys | Asp | Ala | Ser | Met | Ala | Tyr | Arg | Pro | Ser | Glu | Thr | Leu | Cys | Gly |
| | 50 | | | | | 55 | | | | | 60 | | | | |
| Gly | Glu | Leu | Val | Asp | Thr | Leu | Gln | Phe | Val | Cys | Gly | Asp | Arg | Gly | Phe |
| 65 | | | | | 70 | | | | | 75 | | | | | 80 |
| Tyr | Phe | Ser | Arg | Pro | Ala | Ser | Arg | Val | Ser | Arg | Arg | Ser | Arg | Gly | Ile |
| | | | | 85 | | | | | 90 | | | | | 95 | |
| Val | Glu | Glu | Cys | Cys | Phe | Arg | Ser | Cys | Asp | Leu | Ala | Leu | Leu | Glu | Thr |
| | | | 100 | | | | | 105 | | | | | 110 | | |
| Tyr | Cys | Ala | Thr | Pro | Ala | Lys | Ser | Glu | | | | | | | |
| | | 115 | | | | | 120 | | | | | | | | |

IGF-II ANALOGUES

This invention relates to analogues of human insulin-like growth factor II (IGF-II) and to nucleic acid coding for them.

Human IGF-II belongs to a family of growth factors that includes insulin, relaxin, and insulin-like growth factor I (IGF-I). Members of the family share limited sequence homology but are presumed to exhibit similar structures on the basis of a conserved pattern of disulphide bond formation (Dafgard et al, *Journal of Cell Science*, 3:53–64 (1984). IGF-I or somatomedin C is a mitogen that mediates the growth-stimulatory effects of growth hormone throughout childhood and adolescence. The role of the related protein IGF-II is more obscure though it has been implicated in regulating brain and muscle development, placental growth and the stimulation of bone and cartilage formation. IGF-II is found at highest levels in bone (1,750 ng/g dry wt.), about a ten fold higher concentration than for IGF-I (190 ng/g dry wt.). Studies involving in situ hybridisation have revealed that both IGF-I and IGF-II mRNA are produced predominantly in cells of mesenchymal origin. This suggests that both IGFs may be involved in paracrine action on multiple cell types throughout development with each IGF having its own spectrum of targets.

The mature form of IGF-II is 67 amino acids in length, its sequence first elucidated by Riner et al, *FEBS Letters*, 89:293 (1978). The mature molecule is derived from a precursor which includes a 19 amino acid signal peptide and an 89 amino acid C-terminal extension. In addition, a variant form of IGF-II has been described that possesses an extra 3 amino acids in the mature protein. The primary structure of IGF-II is shown in FIG. 1 (SEQ ID NO. 1).

The effects of IGF-II on cells are mediated by at least three different receptors. It has a high affinity for the type I IGF receptor, a membrane bound tyrosine kinase with similar organisation to the insulin receptor. Along with IGF-I, it is likely that the bulk of its effects are mediated by this receptor. IGF-II also binds with high affinity to the type II IGF receptor, a membrane bound protein recently identified as the lysosomal mannose-6-phosphate acceptor (Tong et al., *Journal of Biological Chemistry*, 263:2585–2588 (1987)). Finally, IGF-II can bind to the insulin receptor, though with lower affinity. It is thought that this last interaction is responsible for the hypoglycaemia caused by certain tumours that secrete large amounts of IGF-II (Daughaday et al., *New England Journal of Medicine*, 319:1434–1440 (1988).

A range of pharmacological effects have been demonstrated for IGF-II, both from in vitro and in vivo studies. In vitro, IGF-II stimulates the proliferation of pre-osteoblasts, inhibits the proliferation of mature osteoblasts and stimulates collagen production by mature osteoblasts. In vivo, by osmotic infusion in the rat at 10 µg/day, IGF-II has been found to increase serum/bone alkaline phosphatase levels, increase tibial periosteal bone formation and bone apposition rate, and increase the vertebral forming surface.

The biological effects of both IGF-I and IGF-II are modulated by a number of binding proteins—see Baxter, R. C., *Comparative Biochemistry and Physiology*, 91B:229–235 (1988). Some of these serve simply as carrier proteins in the serum and amniotic fluid. Others, which are more tissue specific in their distribution, are inhibitory and probably function as autocrine or paracrine regulators of cell growth.

The following patent publications cover various aspects of IGF-II:

1. GB-A-0216375 (Amano Pharmaceutical Co. Ltd.) discloses the production of IGF-II by culturing pituitary cells from a patient with acromegaly.

2. EP-A-0135094 (Amgen) discloses the amino acid sequence of IGF-I and IGF-II and nucleotide sequences of genes encoding them. Various hypotheses for their utility are put forward but nothing concrete by way of clinically useful activity is proposed, at least for IGF-II, other than the treatment of pituitary dwarfism.

3. WO-A-8600619 and EP-A-0189481 (Chiron Corporation) disclose prepro-IGF-I and prepro-IGF-II, but again gives no clinical utility for the end peptides.

4. EP-A-0193112 (Columbia University) discloses cDNA encoding IGF-II. Again no specific clinical utility is disclosed or forecast for IGF-II.

5. EP-A-0280460 (Eli Lilly) discloses the use of IGF-II in topical wound healing compositions at a dose which does not produce a systemic insulin-like effect (i.e. does not effect serum glucose levels).

6. EP-A-0128733 (Genentech) discloses the production of 'various forms' of human IGF and EGF by recombinant DNA technology. There is no specific disclosure of clinical utility beyond saying that human IGF can be used as a human growth factor.

7. WO-A-8905822 and EP-A-346429 (GroPep) disclose peptide analogues of IGF-I or IGF-II in which at least the glutamic acid residue is absent at position 3 from the N-terminal of IGF-I or at position 5 or 6 from the N-terminal of IGF-II.

8. WO-A-9015142 (GroPep) discloses the production of IGF-I or IGF-II fusion proteins using suitable expression vectors.

9. EP-A-0230869 (Kabigen AB) discloses the use of cDNA coding for immunoglobulin-G binding domains which are useful in the production of transformed hosts for production of foreign proteins such as IGF-I and IGF-II.

10. EP-A-0361956 (Eli Lilly) discloses DNA sequences encoding for protein derivatives such as IGF-I, IGF-II which can be produced in a natural form without non-natural amino acids.

11. EP-A-0224885 (Wakunaga Seiyaku Kabushika Kaisha) discloses the use of growth factors (EG, IGF-II) for enhancing antitumour actions of antitumour agents or treatments including those against which tumour or cancer has acquired resistance or reduces side effects due to the antitumour agents or treatments.

A number of approaches to the production of both IGF-I and IGF-II have been described. IGFs were originally purified from human serum, and IGF-II has been produced by cell culture. The potential advantages of using a recombinant DNA approach led a number of groups to investigate the expression of IGFs in *E. coli* and yeast. Production of recombinant IGF-I was successfully demonstrated in yeast by secretion as a fusion with the leader and pro-sequences from the *S. cerevisiae* α-factor mating hormone (see for example Shuster et al., *Gene*, 83:47–55 (1989)). High level production of IGF-I from *E. coli* was achieved by employing a protein A/IGF-I fusion which directed the secretion of the fused product into the periplasmic space (Moks et al., *Bio/Technology*, 5:379–382 (1987)). The fusion protein could be isolated by virtue of the affinity of the protein A tail for an immunoglobulin column, and the mature IGF-I released by treatment with hydroxylamine. Both of these methods give rise to correctly folded material. Both methods, however, are associated with problems. The yeast derived material is subject to variable amounts of O-linked glycosylation (Hard et al., *FEBS Letters*, 248:111–114 (1989), and the *E. coli*-derived material contains a number of contaminants including proteolytically nicked, oxidised and norleucine containing forms (Forsberg et al., *Biochemical Journal*, 271:357–363 (1990).

Production of recombinant IGF-II has proved more problematic. Its successful production in yeast has not been described. Our own experience, using a similar approach to that described above for IGF-I, is that only very low level secretion can be obtained, probably due to proteolysis in the ER or golgi apparatus. Similarly, secretion from *E. coli* results in far lower levels of product than can be obtained with IGF-I. This again has been shown to be due to proteolysis, primarily within the C region of the molecule (Hammarberg et al., *PNAS*, 86:4367–4371 (1989)). Full length IGF-II can be obtained by secretion from *E. coli* if a dual fusion approach is employed (ibid). This involves an N-terminal protein A fusion, to direct secretion of the material, and a C-terminal fusion to a region of the Staphylococcal protein G receptor that mediates binding to human serum albumin (HSA). This C-terminal fusion provides some protection against proteolysis and allows for selective purification of full-length material by passage down a column carrying immobilised HSA. This strategy is elegant but complex, and requires additional steps to cleave the IGF-II from the fusion tails. Furthermore, the use of CNBr to cleave the C-terminal tail leaves a modified C-terminus carrying homoserine or homoserine lactone. Another successful strategy has been to produce IGF-II intracellularly as a fusion protein carrying 45 amino acids from the trp leader and trpE polypeptide (Furman et al., *Bio/Technology*, 5:1047–1051 (1987)). The high level expression of this protein directed by a trp promoter construct leads to its accumulation as inclusion bodies. This affords protection against proteases and simplifies the initial steps of the purification. The authentic material can be obtained after CNBr cleavage of the fusion protein and refolding under controlled conditions to allow for the correct formation of disulphide bonds. None of these approaches to the production of IGF-II is ideal, however, because of the problems associated with proteolysis. In particular, the complexities introduced by the necessity for chemical cleavage and/or refolding steps makes them less than suitable as production processes. An ideal approach would be the direct production of correctly folded material by high level secretion from a widely used host such as *E. coli*.

There is much interest in the use of IGFs in the treatment of growth disorders, osteoporosis and other osteopaenias, muscle wasting diseases and wound healing. It is therefore of considerable utility to produce new forms of IGF with improved production characteristics and enhanced biological properties. In particular the sensitivity of IGF-II to proteases and its tendency to induce insulin-like effects at high doses are real obstacles to its therapeutic use.

The invention seeks to solve the problems of providing an improved method for producing IGF-II and of providing engineered forms of IGF-II with improved pharmacological properties. It has been discovered that certain mutants in the C region of IGF-II were no longer cleaved on secretion from *E. coli*, and that whilst they retained activity, and at least in some cases full activity, on the type I and type II IGF receptors, they exhibited lower, at least in some instances 10-fold lower, affinity for the insulin receptor. This was a surprising result, not predicted from modelling studies.

According to a first aspect of the invention, there is provided an Insulin-like Growth Factor II (IGF-II) analogue in which at least one of R37 and R38, wherein R37 represents the natural arginine residue at position 37 and R38 represents the natural arginine residue at position 38, is replaced with another amino acid residue.

Preferably, both R37 and R38 are replaced. If they are both replaced, they need not be replaced with the same amino acid residue, although it may be preferred for both replacement amino acid residues to be the same in at least some circumstances.

It is preferred that the or each replacement amino acid residue be non-basic. Non-basic residues include:

| | | |
|---|---|---|
| Alanine | Ala | A |
| Valine | Val | V |
| Leucine | Leu | L |
| Isoleucine | Ile | I |
| Proline | Pro | P |
| Phenylalanine | Phe | F |
| Tryptophan | Trp | W |
| Methionine | Met | M |
| Glycine | Gly | G |
| Serine | Ser | S |
| Threonine | Thr | T |
| Cysteine | Cys | C |
| Tyrosine | Tyr | Y |
| Asparagine | Asn | N |
| Glutamine | Gln | Q |
| Aspartic acid | Asp | D and |
| Glutamic acid | Glu | E. |

Basic residues apart from arginine (Arg, R) include lysine (Lys, K) and Histidine (His, H).

Preferred non-basic residues are the neutral residues (i.e. those other than Asp and Glu) and those other than Pro. The amide residues (Asn and Gln, particularly Gln) are the most preferred. IGF-II with the modifications Arg37Gln and Arg38Gln (SEQ ID NO.2) is a good example of this aspect of the invention.

Other particular examples include:

| | |
|---|---|
| Arg 37 | Arg 38 Gln |
| Arg 37 | Arg 38 His |
| Arg 37 | Arg 38 Pro |
| Arg 37 Pro | Arg 38 |
| Arg 37 | Arg 38 Ala |
| Arg 37 Ser | Arg 38 |

Apart from the above modifications, a limited number of other modifications may be made to the natural IGF-II sequence, provided that the required biological activity is not lost. For example, up to five further amino acid residues may be modified by way of replacement, addition or deletion, although it is preferred that only one or two other amino acid residues be modified. Of course, in some circumstances it may be appropriate to couple an IGF-II analogue to a proteinaceous carrier, in which case a large number of additional amino acid residues, attributable to the carrier, may be present.

IGF-II analogues in accordance with the invention may in principle be made by any appropriate means. In general, therefore, according to a second aspect of the invention, there is provided a process for preparing an IGF-II analogue as described above, the process comprising coupling together successive amino acid residues and/or ligating oligo- and/or poly-peptides. Most conveniently, recombinant DNA technology is used to prepare the IGF-II analogues in an appropriate host cell; in these circumstances, successive amino acid residues will be coupled together ribosomally under the direction of nucleic acid, which also forms part of the invention.

According to a third aspect of the invention, there is provided nucleic acid coding for an IGF-II analogue as described above. The nucleic acid will usually be DNA, but RNA is also within the scope of the invention. DNA in accordance with this aspect of the invention will usually be synthetic or recombinant and may, but will not necessarily, be in isolated form.

Recombinant DNA in accordance with the invention may be in the form of a vector. The vector may for example be a plasmid, cosmid or phage. Vectors will frequently include one or more selectable markers to enable selection of cells transfected (or transformed: the terms are used interchangeably in this specification) with them and, preferably, to enable selection of cells harbouring vectors incorporating heterologous DNA. Appropriate start and stop signals will generally be present. Additionally, if the vector is intended for expression, sufficient regulatory sequences to drive expression will be present. Vectors not including regulatory sequences are useful as cloning vectors.

Cloning vectors can be introduced into *E. coli* or another suitable host which facilitate their manipulation. According to another aspect of the invention, there is therefore provided a host cell transfected or transformed with DNA as described above.

DNA in accordance with the invention can be prepared by any convenient method involving coupling together successive nucleotides, and/or ligating oligo- and/or polynucleotides, including in vitro processes, but recombinant DNA technology forms the method of choice.

According to a fourth aspect of the invention, there is provided a process for the preparation of nucleic acid as described above, the process comprising coupling together successive nucleotides and/or ligating oligonucleotides. IGF-II analogues in accordance with the first aspect of the invention may be medically useful. According to a fifth aspect of the invention, there is therefore provided an IGF-II analogue as described above for use in medicine, particularly in the treatment of growth disorders, osteoporosis and/or other osteopaenias, muscle wasting diseases and/or wound healing.

According to a fifth aspect of the invention, there is provided the use of an IGF-II analogue in accordance with the first aspect in the manufacture of a medicament for use in the treatment of growth disorders, osteoporosis and/or other osteopaenias, muscle wasting diseases and/or wound healing. It win be appreciated that the invention can be used in a method for the treatment or prophylaxis of growth disorders, osteoporosis and/or other osteopaenias, muscle wasting diseases and/or wound healing, the method comprising administering to a subject an effective amount of an IGF-II analogue as described above.

According to a sixth aspect of the invention, there is provided a pharmaceutical composition comprising an IGF-II analogue as described above and a pharmaceutically acceptable carrier therefore.

Appropriate pharmaceutical compositions and formulations can be prepared by those skilled in the art. Since pharmaceutical compositions in accordance with the invention contain proteins, they will generally be administered parenterally, for example by injection (whether intravenous, subcutaneous or intramuscular) or by implantation. For this reason compositions of the invention will generally be sterile. Suitable carriers may include water for injections and phosphate-buffered saline. Dosages will generally be determined by the physician or clinician.

Another aspect of the invention relates to solving the problem of how to produce natural IGF-II or an analogue, whether as described above or not, in *E. coli*. It has been discovered that if the IGF-II or analogue is expressed in *E. coli* as a fusion protein with at least a part of horseradish peroxidase (HRP), the difficulties caused by degradation are much reduced. HRP is particularly useful because it is expressed at high levels in *E. coli* and forms inclusion bodies and because a synthetic gene for HRP has been described (WO-A-8903424) and is commercially available (British Bio-technology Limited, Laboratory Products Division, Abingdon, Oxfordshire, UK). The fusion protein produced can be cleaved (for example with cyanogen bromide) and the IGF-II or analogue recovered.

In a seventh aspect, the invention therefore provides a process for the production of Insulin-like Growth Factor II (IGF-II), or an analogue thereof, the process comprising culturing *Escherichia coli* containing an expressible gene coding for a fusion protein, wherein the fusion protein comprises at least part of the sequence of horseradish peroxidase cleavably linked to IGF-II or an analogue thereof, under such conditions as to allow the said gene to be expressed, cleaving the fusion protein so formed and recovering the IGF-II or analogue.

The part of the sequence of HRP will generally be sufficient for inclusion bodies to be formed. The N-terminal may be included. Preferably, when cyanogen bromide is to be the cleavage agent, the HRP sequence does not contain any methionine residues except adjacent to the IGF-II or analogue sequence, to ensure unique cleavage. The first 53 amino acids of HRP have been found to be suitable. Of course, this arrangement is not essential, as cleavable linkages can easily be engineered between the HRP and IGF-II (or analogue) sequences.

IGF-II analogues which can be produced by means of this aspect of the invention are those which do not differ in material respects (as far as this production process is concerned) from natural IGF-II. In general no more than ten, and preferably no more than five, amino acid changes from the natural sequence will be present. Particular IGF-II analogues which can be produced by the process of this aspect of the invention include those of the first aspect.

An eighth aspect of the invention provides an *E. coli* expression vector comprising expressible DNA encoding a fusion protein, wherein the fusion protein comprises at least part of the sequence of horseradish peroxidase cleavably linked to IGF-II or an analogue thereof. Host cells containing such a vector also form part of the invention.

Preferred features of each aspect of the invention are as for each other aspect, muatatis mutandis.

The invention will now be illustrated by the examples. The examples refer to the accompanying drawings, in which:

FIG. 3 shows a synthetic gene for IGF-II;

FIG. 5A and 5B shows the strategy used for IGF-II mutagenesis;

Figure 7A:
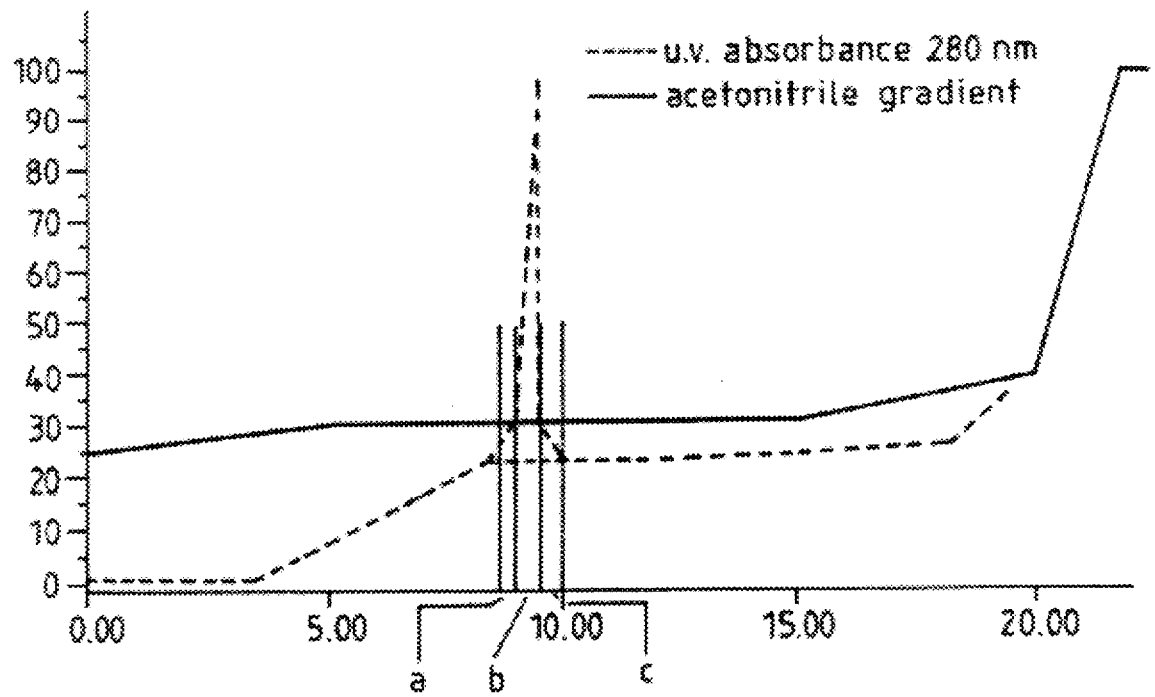
Figure 7B:
Figure 8:
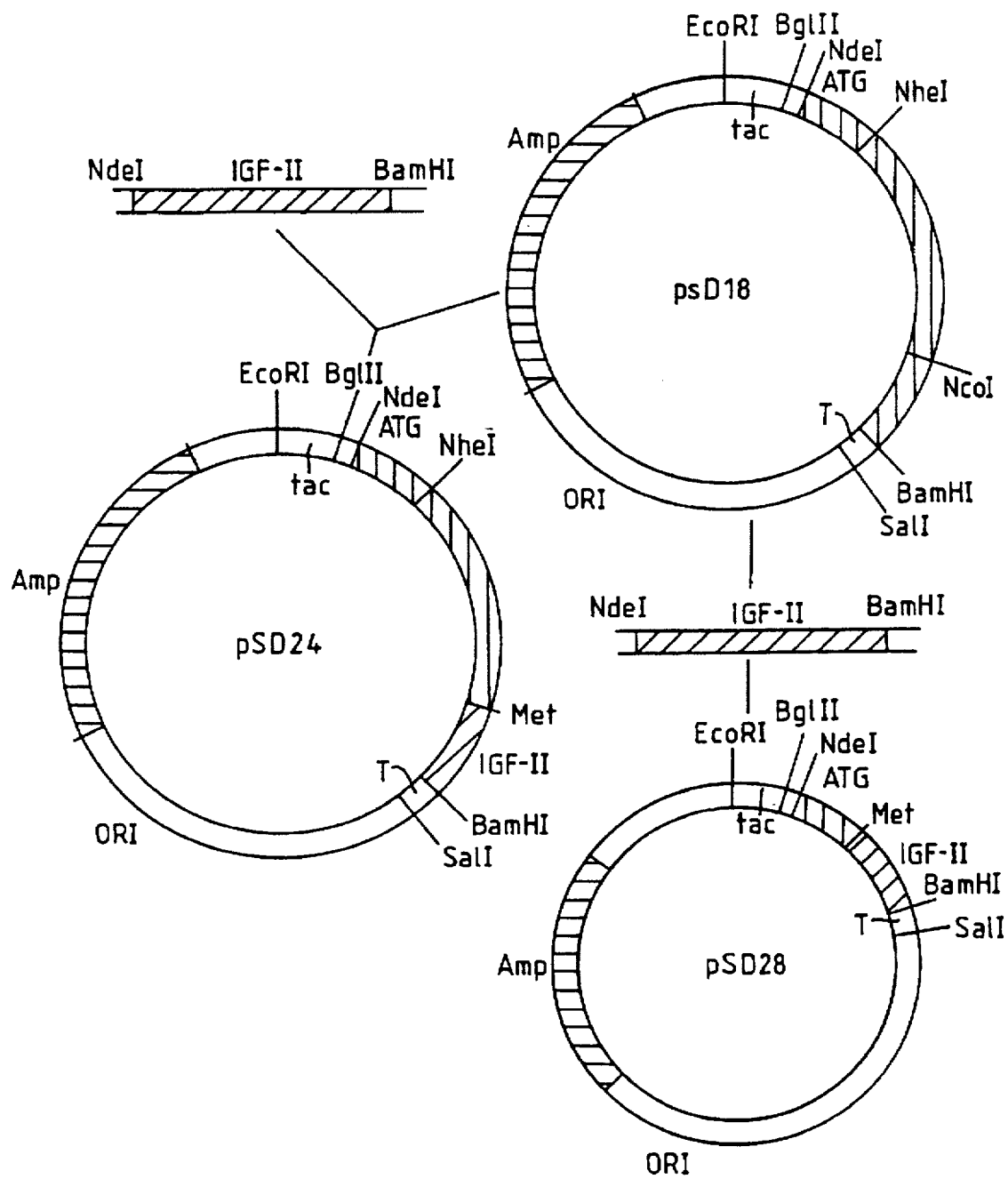

FIG. 7A-B show the purification of IGF-II ($Q^{37}Q^{38}$);

FIG. 8 shows the construction of plasmid pSD28.

Figure 9A:
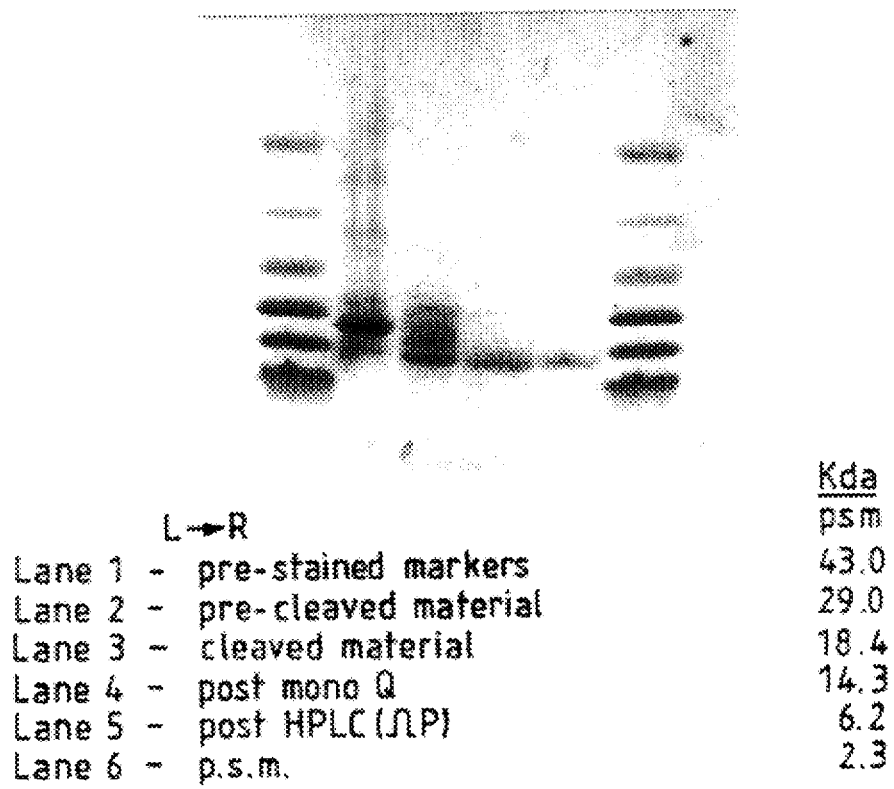
Figure 9B:
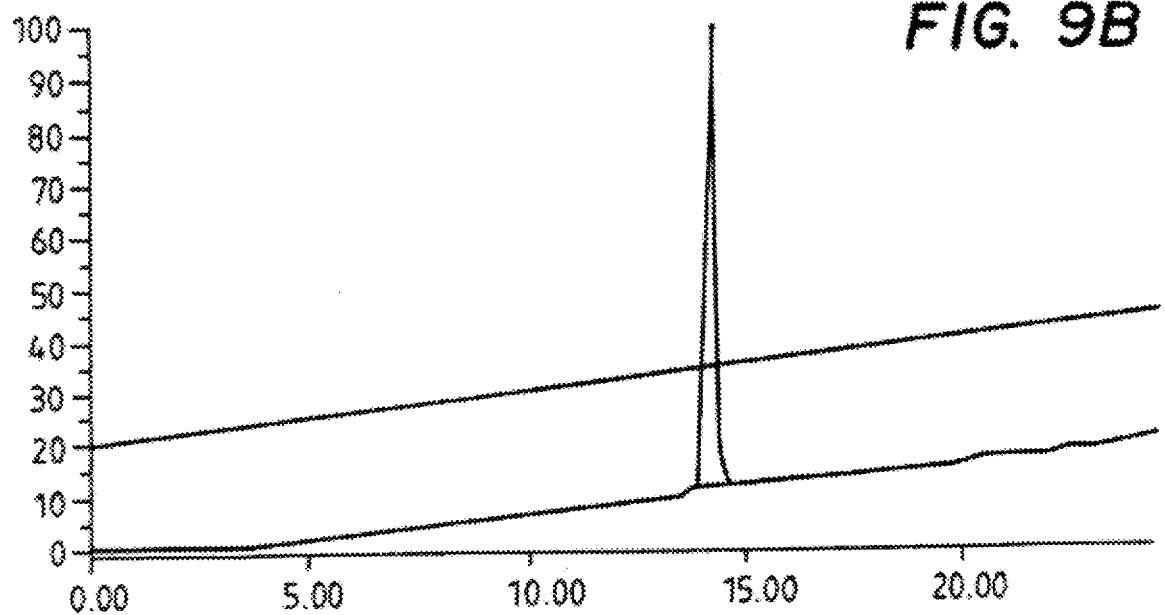
Figure 10:
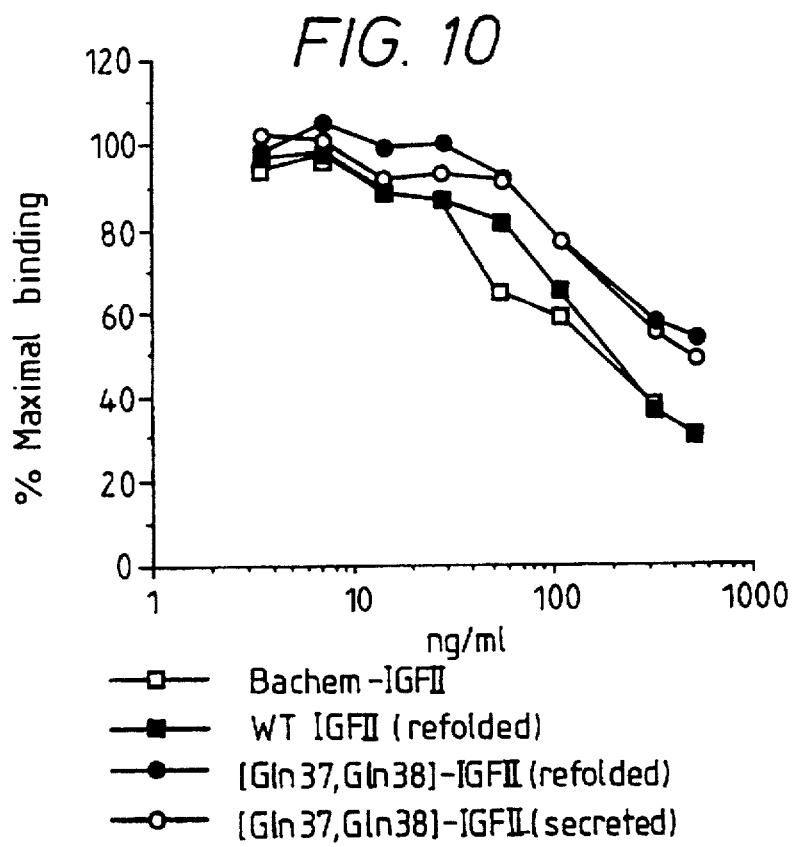
Figure 11:
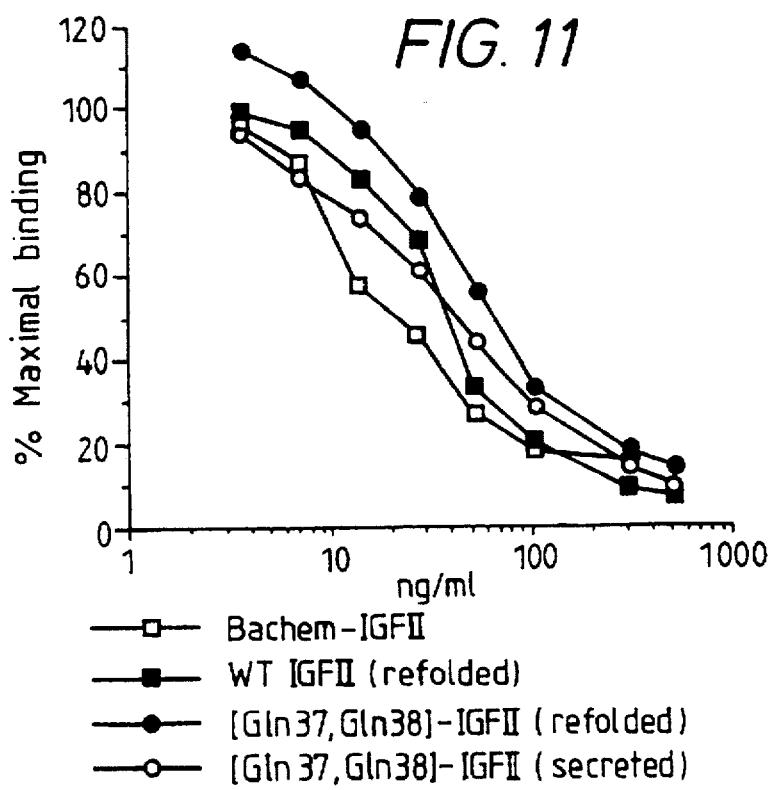
Figure 12:
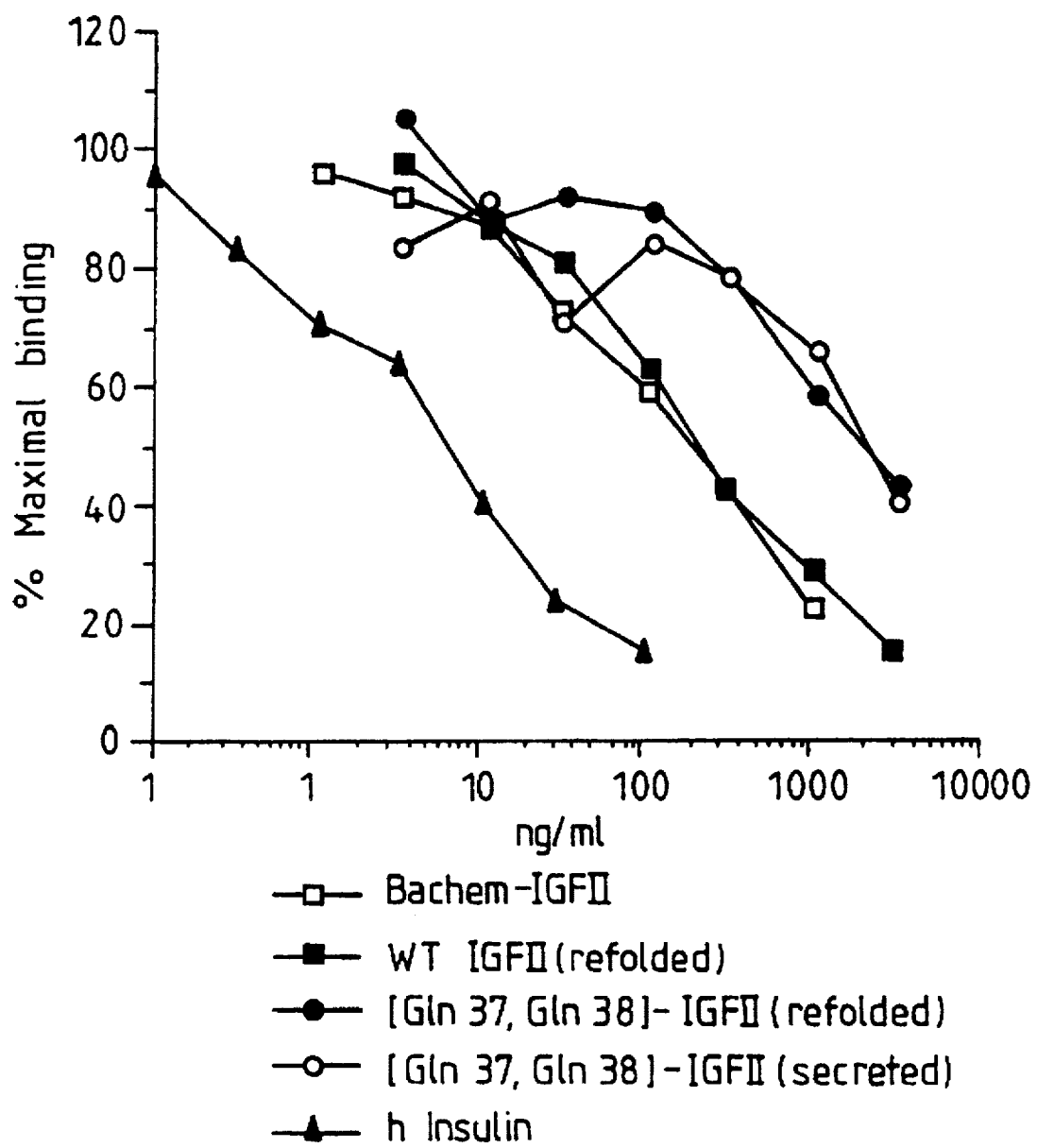

FIG. 9A and 9B shows the purification of IGF-II by the HRP fusion route;

FIG. 10 shows the performance of IGF-II and analogues in accordance with the invention in a Type 1 IGF receptor binding assay;

FIG. 11 shows the performance of IGF-II and analogues in accordance with the invention in a Type 2 IGF receptor binding assay; and FIG. 12 shows the performance of IGF-II and analogues in accordance with the invention in an insulin receptor binding assay.

EXAMPLES

Example 1

Construction of IGF-II Derivatives Carrying Mutations at R37 and R38

Figure 1:
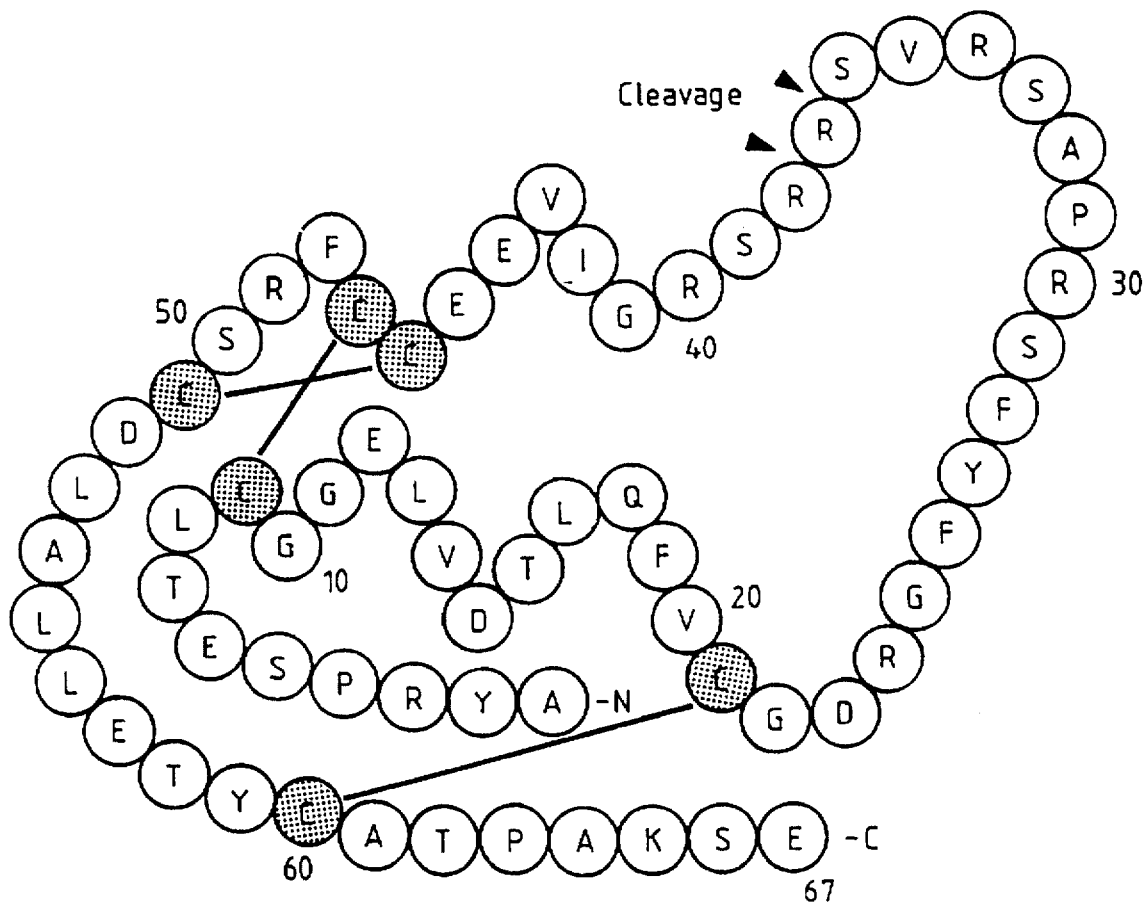
FIG. 1 shows the primary structure of IGF-II.
Figure 2:
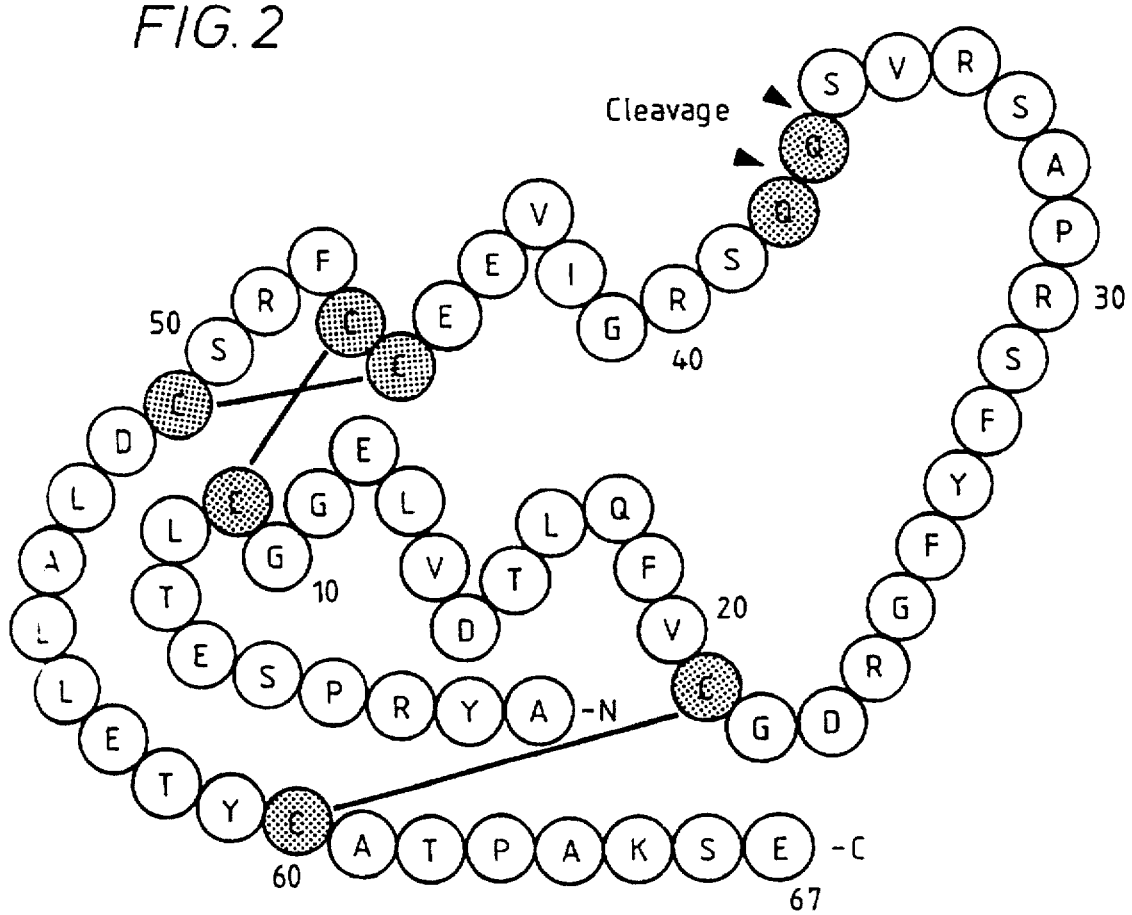
FIG. 2 shows the primary structure of IGF-II ($Q^{37}Q^{38}$)
Figure 4:
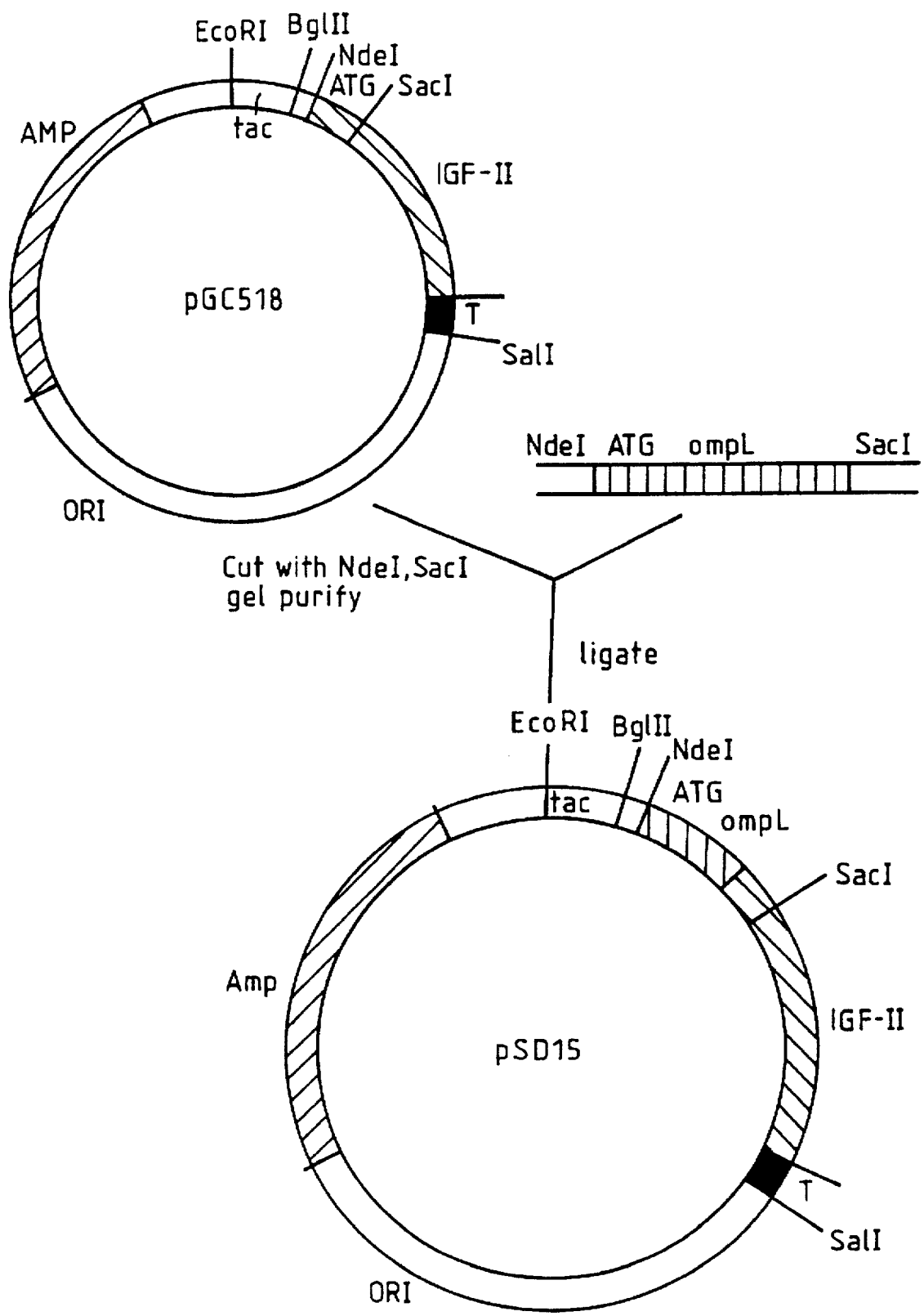
FIG. 4 shows the construction of pSD15.

The sequence of a synthetic gene for IGF-II (SEQ ID NO. 3) is depicted in FIG. 3. The synthesis of this gene has been described in detail in WO-A-8903423. The synthetic gene was cloned as a NdeI/BamHI fragment into the *E. coli* expression vector pGC517 to give pGC518. In order to direct the secretion of IGF-II, an adapter was synthesised that encoded the leader sequence for the ompA gene product (SEQ ID NO. 5). The adapter consisted of two complementary oligonucleotides of 102 and 96 base pairs which upon annealing result in the formation of NdeI and SacI cohesive ends. This adapter was cloned between the NdeI and SacI sites of pGC518 to give the IGF-II secretion vector pSD 15. As secretion vectors are known to be toxic in *E. coli*, the clone was isolated in the lacI$^q$ strain HW1110 to minimise expression in the absence of inducer. The plasmid was re-isolated and the nucleic acid sequence of the ompA and IGF-II regions confirmed. The plasmid was also transformed into JM103; this strain was deposited on 5th Dec. 1990 at the National Collection of Industrial and Marine Bacteria Limited, 23 St. Machar Drive, Aberdeen, AB2 1RY and given accession number NCIMB 40342. FIG. 4 details the construction of pSD15.

IGF-II variants carrying mutations at position Arg37 and/or Arg38 were constructed by site-directed mutagenesis. An M13mp18 derivative carrying IGF-II was constructed by cloning a BgI/II-SalI fragment encompassing IGF-II and the ompA leader from pSD15 between the BamHI and SalI sites in the polylinker. Single stranded DNA was isolated and used as a template in the mutagenesis procedure. Two primers were used. The first, BB1551 (5'-CCTCTAGATTGCTGAGATACACG-3', SEQ ID NO. 7), was a 23mer that directed the substitution of Arg37 and Arg38 with glutamine residues (R37Q, R38Q). The second primer, BB1550 (5'-GCCTCTAGANNNNNNNAGATACACG-3', SEQ ID NO. 8), was a 24mer that directed the randomisation of the residues Arg37 and Arg38. This was achieved by incorporating all four nucleotides during the synthesis cycle at the six bases that are complementary to the two arginine codons. Following the mutagenesis, mutant plaques were identified by growing small isolates of phage from each, purifying single stranded DNA and dideoxy sequencing using M13 universal primer. With BB1551, a mutant incorporating the desired mutation was identified. With BB1550, 11 mutant isolates were obtained carrying various substitutions at Arg36, Arg37 or both positions. The sequence of these mutations is summarised in Table 1. All mutant clones were plaque-purified and used to infect larger cultures of JM103. This allowed the isolation of double stranded replicative form (RF) DNA from each of the mutant isolates.

TABLE 1

BB 1550 and 1551 IGFII Mutations

| Constr. No. | Primer | Mid Selection of Lower Strand Primer | Amino Acid Change |
|---|---|---|---|
| pSD41 | BB1550 | AGA.GTCGTT.AGA | gln gln |
| pSD42 | BB1551 | AGA.GCGGTT.AGA | arg gln |
| pSD43 | BB1551 | AGA.GCGGTA.AGA | arg his |
| pSD44 | BB1551 | AGA.GCTGGA.AGA | arg pro |
| pSD45 | BB1551 | AGA.GGGGCG.AGA | pro arg |
| pSD46 | BB1551 | AGA.GCGCGT.AGA | arg ala |
| pSD47 | BB1551 | AGA.TCGGCG.AGA | ser arg |
| pSD48 | BB1551 | AGA.GATGGC.AGA | leu pro |
| pSD49 | BB1551 | AGA.GCGATA.AGA | arg tyr |
| pSD50 | BB1551 | AGA.GCTFAA.AGA | arg leu |
| pSD51 | BB1551 | AGA.GGGGCT.AGA | pro arg |
| pSD52 | BB1551 | AGA.CGGCAT.AGA | ala val |
| BB 1550 sequence | | CGACATAGA.nnnnnn.AGATCTCCG | |
| BB 1551 sequence | | GCACATAGA.GTCGTT.AGATCTCC | |

The mutations were introduced into the IGF-II expression vector by isolating them from the mutant RF preparation on a NdeI-SalI fragment which was then cloned the NdeI and SalI sites of pSD 15. The identity of the mutations was then re-confirmed by dideoxy sequencing. All the mutant derivatives of pSD15 were then transformed into *E. coli* strain HW1110 (lacI$^q$) for expression studies. The mutagenesis strategy is summarised in FIG. 5.

Example 2

Expression of IGF-II and Mutant Derivatives by Secretion from *E. coli*

The expression of wild-type IGF-II and its mutant variants was assessed by pulse chase analysis. Single colonies were picked and used to inoculate 5 ml of M9 medium containing 100 µg/ml carbenicillin. The cultures were incubated at 37° overnight. In the morning, 200 µl of the saturated cultures was used to inoculate 10 ml of fresh M9 medium, and incubated with shaking until the optical density at 670 nm reached 0.45. A 5 ml aliquot of each culture was then transferred to a fresh universal tube and induced by the addition of 50 µl of 0.5M IPTG. The cultures were shaken for a further 60 min at 37°. Each culture was then pulse-labelled by the addition of $^{35}$S-cysteine to a final concentration of 20 µCi/ml. The cultures were incubated for a further 5 min, after which the labelling was terminated by the addition of 100 µl of cold L-cysteine at 5 mg/ml. The incubation was continued for a further 15 min. The cell concentration was determined by measuring the O.D. at 670 nm and the cultures were then divided into 1 ml aliquots, the cells collected by centrifugation at 10,000 rpm for 1 min in a Microfuge (microcentrifuge), the supernatants decanted and the cell pellets frozen on dry ice and stored at −70° C.

The cell pellets were treated to release soluble proteins as follows: The pellets were resuspended in ice-cold resuspension buffer comprising 50 mM TRIS pH 8.0, 50 mM NaCl, 0.2 mM PMSF to give a cell concentration equivalent to 10 absorbance units per ml of cells based on the final cell concentration determined at the completion of the pulse chase. Lysozyme solution was then added to a final concentration of 0.2 mg/ml and the cells incubated on ice for 15 min. The cells were then subjected to three cycles of freeze-thaw using a dry ice/methanol bath and a water bath at 25°. The cell lysates were centrifuged at 15,000 g for 30 min to pellet the cell debris and any insoluble material. The supernatants were transferred to a fresh micro-testtube and stored frozen at −20°.

For SDS PAGE analysis of the cell lysates, 10 µl of each supernatant was mixed with 5 µl of sample buffer comprising 6M urea, 10% v/v glycerol, 5% v/v b-mercaptoethanol, 3% w/v SDS, 60 mM TRIS pH 6.8, 0.01% v/v bromophenol blue. The tubes were tightly sealed and incubated at 100° C. for 5 min. Gel electrophoresis was performed with 1 µl of sample on a Phast gel system (Pharmacia) using commercially available 8–25% Phast (Trade Mark) gradient gels. Pre-labelled MW size standards (Amersham) were also run on each gel. After electrophoresis, the gel was fixed in 7% v/v acetic acid, soaked in Amplify (Trade Mark of Amersham), air dried and exposed to X-ray film (Fuji).

Figure 6A:
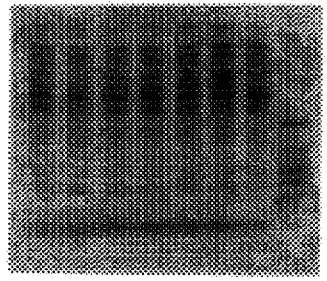
FIG. 6A and 6B shows the expression of IGF-II and mutant variants.
Figure 6B:
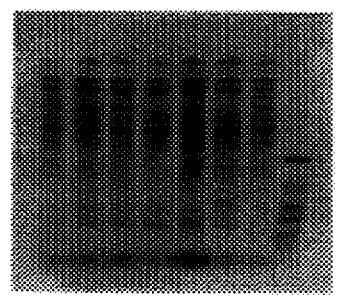

The results are depicted in FIGS. 6A and 6B. Cultures carrying the IGF-II expression plasmid pSD15 (wild-type IGF-II) show a band of between 3–4000 Da which is not present in control cultures (uninduced or without insert). There is no band present at 6–7000 Da, the expected size of IGF-II. In contrast, all the cultures expressing IGF-II mutant derivatives carrying substitutions at either Arg36 or Arg37 or both, exhibited an intense band of the expected molecular weight. The mutants did not show a band at the same location as the degraded IGF-II expressed from pSD15. Furthermore, a preliminary investigation of the receptor binding properties of the soluble extracts indicated that all of the mutants retained at least some biological activity—see Table 2. It was concluded that mutation at Arg36 or Arg37 prevented degradation of the IGF-II by E. coli periplasmic proteases.

Example 3
Production and Purification of IGF-II ($Q^{37}Q^{38}$)

The properties of the protease resistant derivative of IGF-II carried on pSD53 ($Q^{37}Q^{38}$) were investigated in more detail. For larger scale production, strain HW1110 carrying pSD53 was streaked on L-agar plates containing 100 µg/ml carbenicillin and incubated overnight at 37°. The following day, a 10 ml culture of M9 minimal medium containing 100 µg/ml carbenicillin was inoculated with a single colony and incubated at 37° overnight. This fresh overnight culture (8 ml) was used to inoculate 500 ml of fresh pre-warmed M9 medium containing 100 µg/ml carbenicillin in a 2 liter baffle flask. The culture was incubated at 37° C. with shaking until the $OD_{650}$ reached 0.4. IGF-II expression was induced at this stage by the addition of 5 ml of IPTG (0.5M). Incubation was continued for a further 2 hr. The cell concentration was then determined by measuring the $OD_{650}$ of the culture. The cells were then harvested by centrifugation at 6500 rpm for 10 min and the supernatant discarded. The cell pellet was kept on ice until it could be processed.

The volume of solution required to carry out the osmotic shock of the cells was calculated as follows:

Volume (ml)=$OD_{650}$X 0.0075X Broth volume (ml)

The calculated volume of cold 20% w/v sucrose, 10 mM TRIS pH 7.5 was then added and the cells gently resuspended. On resuspension, 0.5M EDTA pH 8.0 was added to give a final concentration of 1 mM. The cell suspension was then incubated for 10 min on ice. The cells were recovered by centrifugation at 6500 rpm for 10 min at 4°. The supernatant was discarded and the cells were rapidly resuspended in the calculated volume of ice cold water. After a further 10 min incubation on ice, the cells were removed by centrifugation at 6500 rpm for 10 min at 4°. The supernatant (periplasmic fraction) was decanted and used for further processing.

Aliquots of the periplasmic fraction, typically 40 ml, were adjusted with 10% v/v trifluoroacetic acid (TFA) to a final concentration of 0.1% v/v TFA. After centrifugation at 3500 rpm for 10 min at 4°, the aliquot was loaded onto a 20 ml preparative Vydac C-18 column pre-warmed-equilibrated in 25% acetonitrile, 0.1% v/v TFA with a flow rate of 4 ml/min. After washing in the same buffer to reduce the background absorbance to a stable base line, the IGF-II was eluted using a linear gradient of 25–40% v/v acetonitrile, 0.1% TFA over 45 min with a flow rate of 4 ml/min. Analysis of the active purified peak using automated N-terminal sequence analysis, analytical reverse phase HPLC and SDS PAGE indicates that the IGF-II ($Q^{37}Q^{38}$) is >95% homogenous—see FIG. 7A.

Example 4
Production of IGF-II and IGF-II ($Q^{37}Q^{38}$) by Expression as Fusion Proteins in E. coli An additional product on route for IGF-II was sought that would allow the production of wild-type material to compare with the IGF-II cleavage resistant mutants. It was decided to produce this material intracellularly in E. coli as a fusion protein; although this approach has been used in the expression of small peptides, them does not have appear to have been any realisation of the particular advantages that flow from adapting the approach to IGF-II production. A system based on horseradish peroxidase (HRP) was developed. HRP is an enzyme which, when expressed at high levels in E. coli, readily forms inclusion bodies—see Smith et al, Journal of biological Chemistry, 265:13,335–13343 (1989).

The synthesis and expression of a synthetic gene for HRP has been described (WO-A-8903424). The HRP expression plasmid pSD18 contains a NdeI-BamHI cassette cloned between the NdeI and BamHI sites of the tac expression vector pGC517. The construction of this plasmid is described in the above patent application. Initially, the IGF-II gene was fused to the C-terminus of HRP by making use of an NcoI site in the HRP coding sequence.

To achieve this, pSD18 was linearised within the HRP gene with NcoI. The 5' cohesive ends were removed by digestion with mung bean nuclease. The linearised plasmid was purified by phenol extraction and ethanol precipitation and subjected to further digestion with BamHI. This provided the vector with a blunt end within the HRP gene and a BamHI cohesive end adjacent to the transcription terminator. A fragment carrying IGF-II was isolated from pGC518 by linearising the plasmid with NdeI, blunt-ending by filling in the recessed ends with Klenow fragment of DNA polymerase, and finally digesting with BamHI. The BamHI/blunt-ended fragment encoding IGF-II was isolated by electrophoresis and ligated into the BamHI/blunt-ended vector fragment obtained from pGC518. The ligation products were transformed into HW 1110 and the desired recombinants identified by restriction analysis of plasmid DNA isolated from individual transformant colonies selected on L-agar plates containing 100 µg/ml carbenicillin. This procedure resulted in the construction of a gene (SEQ ID NO. 9) encoding a fusion protein comprising the first 282 aminoacid residues of HRP fused to IGF-II via a methionine residue to allow for the release of mature IGF-II by cleavage with cyanogen bromide. The fusion protein lacks the final 27 amino acids of HRP. The plasmid carrying this fusion gene was designated pSD24.

The fusion protein encoded by pSD24 was not ideal for the production of IGF-II for two reasons. First, the IGF-II is only 19% of the total fusion protein. Second, and more important, the HRP portion of the molecule contains an additional two internal methionine residues. This results in the generation of additional fragments on CNBr cleavage, similar in size to IGF-II, and complicates the isolation procedure. A fusion protein was therefore engineered that carrier less residual HRP sequence. This was achieved by a similar process to that used in the construction of pSD24, except that an NheI site within the HRP gene was used instead of the NcoI site. Plasmid pSD18 was linearised with NheI, the recessed ends were filled in with Klenow fragment of DNA polymerase I, and finally digested with BamHI. The NdeI-BamHI fragment carrying IGF-II was isolated from pGC518, and the NdeI site blunt-ended, as described above. The linearised pSD18 vector and the IGF-II carrying fragment were separated on low-gelling temperature gels, isolated by phenol extraction and ligated together. The ligation products were transformed into NW1110 and the desired recombinants identified by restriction analysis of plasmids isolated from individual transformants. The integrity of the junctional sequences was confirmed by dideoxy DNA sequencing. This procedure resulted in a gene encoding a fusion between the first 53 amino acids of HRP and mature IGF-II linked by a unique methionine residue (SEQ ID NO. 11). This plasmid was designated pSD28—see FIG. 8.

For production of fusion protein, an overnight culture was prepared by inoculating 10 ml of M9 minimal medium containing 100 µg/ml carbenicillin with a single colony of HW1110/pSD28. The culture was incubated at 37° with shaking for about 18 hr. (overnight). The overnight culture was then used to inoculate 8×500 ml aliquots of pre-warmed M9 minimal medium containing 100 µg/ml carbenicillin in 2 liter baffle flasks. The cultures were incubated at 37° with shaking until the cell density measured by $O.D._{670}$ reached 0.3–0.4. Expression of the fusion protein was induced by the addition of 5 ml of 0.5M IPTG per flask, and the incubation continued for a further 4 hr. The cells were then collected by centrifugation at 6,500 rpm for 10 min and the supernatants discarded. The cell pellets were then either processed immediately or stored at −70° until needed.

Each pellet from 500 ml of culture was then treated as follows: the cells were resuspended in 50 ml of ice-cold 50 mM TRIS pH 8.0, 50 mM NaCl, 1 mM EDTA. Lysozyme was then added to a final concentration of 1 mg/ml and the cells kept on ice for 20 min. To complete the lysis, 2.75 ml of sodium deoxycholate 2% w/v was added and the cells were incubated for 5 min at 37°. The preparation was then cooled and sonicated until no longer viscous. The sample was then centrifuged at 15,000 rpm for 20 min to pellet the inclusion bodies. The supernatant was discarded and the pellets containing the fusion protein resuspended and washed three times in 50 ml of a buffer comprising 0.05% Triton X100, 0.1 mM PMSF, 10 mM EDTA pH 8.0 and three times in 50 ml 3M urea, 50 mM TRIS pH 8.0. At this stage the inclusion bodies were weighed and resuspended to 10 mg/ml in formic acid 75% v/v containing sodium thiosulphate at 3% w/w of inclusion bodies. An approximately 10 fold molar excess of cyanogen bromide (about 50 mg) was then added in a fume hood and the sample incubated overnight at room temperature with gentle mixing (after the method described in U.S. Pat. No. 4,451,396). The sample was then dried by rotary evaporation, washed once with an equal volume of water, dried and resuspended in 7M urea, 50 mM TRIS pH 8.0 to a final concentration of 10 mg/ml inclusion bodies. Sodium sulphite and sodium tetrathionate were added to final concentrations of 100 mM and 10 mM respectively and the sample allowed to stand at room temperature to effect sulphitylation of cysteine residues.

The derivatised IGF-II was then purified by ion-exchange chromatography on a Mono Q (Trade Mark) column, loading in 50 mM TRIS pH 8.0, 7M urea. The material was eluted with a gradient of 0–400 mM NaCl in the same buffer over 10 column volumes. The peak containing IGF-II as determined by gel analysis was chromatographed on a PD-10 size exclusion column in 20 mM glycine, 1M urea pH 10.0 to effect buffer exchange. Cysteine was added to achieve an approximately 4-fold molar excess over protein, equivalent to a final concentration of about 100 µg/ml, and the mixture allowed to stand for 16 hr. at 4°. The reaction was quenched by the addition of 1M HCl to a final pH of about 2.5 and the sample loaded onto a Dynachrome FPLC cation exchange column equilibrated in 20 mM malonic acid, 1M urea pH 2.5. The IGF-II was eluted with a gradient of 0–2M NaCl in the same buffer over 10 column volumes. The active, refolded IGF-II fraction was then subjected to buffer exchange into 0.1% w/v TFA on a PD-10 column and subsequently loaded onto a Vydac analytical reverse phase C-18 HPLC column and eluted with a gradient of 20–45% acetonitrile, 0.1% w/v TFA over 20 min at a flow rate of 1 ml/min. Analysis of the active purified peak using automated N-terminal sequence analysis, analytical reverse phase HPLC and SDS PAGE indicates that the IGF-II is >95% homogenous—see FIG. 9B.

The fusion/renaturation approach was also used to produce IGF-II ($Q^{37}$,$Q^{38}$). To construct a derivative of pSD28 carrying the Q37 and Q38 mutations, a Bg/II-SalI fragment encompassing all of the HRP-IGF-II fusion was cloned into BamHI/SalI-cut M13mp18. Single strands were prepared and site directed mutagenesis performed with primer BB1551 as described in Example 1. Phage carrying the desired mutation were identified by DNA sequence analysis on small scale single stranded DNA preparations from individual plaques. An isolate carrying the desired R37Q, R38Q mutations was identified and RF DNA prepared. The cassette encoding the mutant fusion derivative was then excised as an NdeI-BamHI fragment and cloned into NdeI/BamHI digested pGC517 to give pSD103. This plasmid is identical to pSD28 except for the presence of the Q37,Q38 mutations.

Inclusion bodies for the HRP/IGF-II ($Q^{37}$,$Q^{38}$ derivative were obtained and the mutant protein purified as described above for wild-type IGF-II. The biological characterisation of the refolded IGF-II, both wild-type and mutant, is described in Example 5.

Example 5
Biological Characterisation of IGF-II ($Q^{37}Q^{38}$)

The properties of the mutant IGF-II (R37Q,R38Q) were compared to those of wild-type material by assessing its ability to bind to the type 1 and 2 IGF receptors and the insulin receptor. The mutant IGF-II was produced either by secretion into the periplasmic space (Example 3) or by intercellular expression as a fusion protein followed by renaturation (Example 4). Two forms of wild-type IGF-II were used for comparison. The fusion route was used to make material directly comparable to the refolded mutant derivative. In addition, recombinant IGF-II from a commercial supplier (Bachem) was used as a reference standard. The protein concentration of the purified homogenous material used for characterisation was determined by measurement of absorbance at 280 nm.

Binding of the peptides to the type 1 IGF receptor on Swiss mouse 3T3 cells is shown in FIG. 10. Swiss 3T3 cells at $5 \times 10^4$ cells/ml were seeded into 24 well plates at $5 \times 10^3$ cells/well in DMEM containing 10% FCS and incubated at 37°. The cells were used for assay after 5–6 days. For the binding assay, the growth medium was flicked out of the plate, and the cells washed twice with binding medium (serum free DMEM containing 25 mM HEPES, 1 mg/ml BSA and 2 mM glutamine). A further 400 µl of binding medium was added to each well along with 50 μl of sample or IGF-II standard (Bachem). Twofold dilutions of IGF-II were used for the standard curve to give final concentrations in the well from 300–1.56 ng/ml. Labelled IGF-I was then added (50 μl of $^{125}$I-IGF-I) to give a final concentration of 1 ng/ml and a total of about 40,000 dpm per well. The plate was incubated at room temperature for 2 hr., the assay medium removed and the cells washed four times in PBS containing 1 mg/ml BSA and 0.1 μM KI. The plates were blotted dry and the cells solubilised for by the addition of 750 μl 0.5M NaOH containing 0.2% w/v Triton X100. After 15 min the lysed samples were transferred to tubes and the residual counts determined using a gamma counter.

The IGF-II ($Q^{37}Q^{38}$) mutant, produced using either the secretion or refolding route, inhibits binding of $^{125}$I-IGF-II with an $IC_{50}$ of 210 ng/ml compared to 60 ng/ml and 100 ng/ml for the wild-type standard (Bachem) and wild-type refolded material respectively.

Binding to the type 2 IGF receptor was assessed on H35 (rat hepatoma) cells, see FIG. 11. Cells at $5\times10^5$ cells/ml were seeded into 24 well plates at $5\times10^4$ cells/well in DMEM containing 0.5% FCS and incubated at 37°. The cells were used for assay after 2–3 days. For the binding assay, the growth medium was flicked out of the plate, and the cells washed once with binding medium (serum free DMEM containing 25 mM HEPES, 1 mg/ml BSA and 2 mM glutamine).

A further 400 μl of binding medium was added to each well along with 50 μl of sample or IGF-II standard (Bachem). Twofold dilutions of IGF-II were used for the standard curve to give final concentrations in the well from 300–1.56 ng/ml. Labelled IGF-II was then added (50 μl of $^{125}$I-IGF-I) to give a final concentration of 2 ng/ml and a total of about 40,000 dpm per well. The plate was incubated at room temperature for 3 hr., the assay medium removed and the cells washed four times in Hanks buffered salt solution containing 1 mg/ml BSA. The plates were blotted dry and the cells solubilised for by the addition of 750 μl 10 mM Tris HCl, 5 mM EDTA, 0.2% w/v SDS. After 15 min the lysed samples were transferred to tubes and the residual counts determined using a gamma counter.

The mutant IGF-II ($Q^{37}Q^{38}$) inhibits the binding of $^{125}$I-IGF-II with $IC_{50}$ values of 30 ng/ml (secreted) and 60 ng/ml (refolded). The wild-type reference standard and the wild-type refolded material gave values of 18 ng/ml and 30 ng/ml respectively in the same assay.

Binding of the peptides to the insulin receptor, also on H35 cells, is shown in FIG. 12. The assay was performed exactly as described for the type 2 IGF receptor except that 125I-insulin was used instead of labelled IGF-II (Amersham). In this assay, the mutant IGF-II ($Q^{37}Q^{38}$) inhibits the binding of $^{125}$I-insulin with $IC_{50}$ values of 1600 ng/ml and 1300 ng/ml for secreted and refolded material respectively. In contrast, the wild-type material exhibits much higher affinity with $ICs_{50}$ values of 130 ng/ml for the standard and 160 ng/ml for the refolded material. Insulin itself has an $IC_{50}$ of 4.8 ng/ml in this assay.

These results show that substitution of glutamine for arginine at positions 37 and 38 of the native IGF-II molecule decreases its affinity for the insulin receptor by 10-fold. In contrast, the affinity of IGF-II ($Q^{37}Q^{38}$) for the types 1 and 2 IGF receptor is comparable to native IGF-II. There is no appreciable difference in activity between material produced using either the secretion or HRP fusion approaches.

METHODS

All the techniques of genetic manipulation used in the manufacture of this gene are well known to those skilled in the art of genetic engineering. A description of most of the techniques can be found in the laboratory manual entitled Molecular Cloning by T. Maniatis, E. F. Fritsch and J. Sambrook published by Cold Spring Harbor Laboratory, Box 100, New York.

Additional and modified methodologies are detailed below.

Oligonucleotide synthesis

The oligonucleotides were synthesised by automated phosphoramidite chemistry using cyanoethyl phosphoramidites. The methodology is now widely used and has been described (Beaucage, S. L. and Caruthers, M. H. Tetrahedron Letters. 24,245 (1981)).

Purification of Oligonucleotides

The oligonucleotides were de-protected and removed from the CPG support by incubation in concentrated $NH_3$. Typically, 50 mg of CPG carrying 1 micromole of oligonucleotide was de-protected by incubation for 5 hr at 70° in 600 μl of concentrated $NH_3$. The supernatant was transferred to a fresh tube and the oligomer precipitated with 3 volumes of ethanol. Following centrifugation the pellet was dried and resuspended in 1 ml of water. The concentration of crude oligomer was then determined by measuring the absorbance at 260 nm.

For gel purification 10 absorbance units of the crude oligonucleotide were dried down and resuspended in 15 μl of marker dye (90% de-ionised formamide, 10 mM tris, 10 mM borate, 1 mM EDTA, 0.1% bromophenol blue). The samples were heated at 90° for 1 minute and then loaded onto a 1.2 mm thick denaturing polyacrylamide gel with 1.6 mm wide slots. The gel was prepared from a stock of 15% acrylamide, 0.6% bisacrylamide and 7M urea in 1 XTBE and was polymerised with 0.1% ammonium persulphate and 0.025% TEMED. The gel was pre-warmed-run for 1 hr. The samples were run at 1500 V for 4–5 hr. The bands were visualised by UV shadowing and those corresponding to the full length product cut out and transferred to microtesttubes. The oligomers were eluted from the gel slice by soaking in AGEB (0.5M ammonium acetate, 0.01 M magnesium acetate and 0.1% SDS) overnight. The AGEB buffer was then transferred to fresh tubes and the oligomer precipitated with three volumes of ethanol at −70° for 15 min. The precipitate was collected by centrifugation in an Eppendorf microfuge for 10 min, the pellet washed in 80% ethanol, the purified oligomer dried, redissolved in 1 ml of water and finally filtered through a 0.45 μm microfilter. The concentration of purified product was measured by determining its absorbance at 260 nm.

Kinasing of oligomers 250 pmole of oligomer was dried down and resuspended in 20 μl kinase buffer (70 mM Tris pH7.6, 10 mM $MgCl_2$, 1 mM ATP, 0.2 mM spermidine, 0.5 mM dithiothreitol). 10 u of T4 polynucleotide kinase was added and the mixture incubated at 37° for 30 min. The kinase was then inactivated by healing at 85° for 15 min.

Isolation of DNA from agarose gels

The volume of the gel slice was estimated from its weight and then melted by incubation at 65° for 10 min. The volume of the slice was then made up to 400 μl with TE (10 mM Tris pH 8.0, 1 mM EDTA) and Na acetate added to a final concentration of 0.3M. 10 μg of yeast tRNA was also added as a carrier. The DNA was then subjected to three rounds of extraction with equal volumes of TE equilibrated phenol followed by three extractions with ether that had been saturated with water. The DNA was precipitated with 2 volumes of ethanol, centrifuged for 10 min in a Microfuge, the pellet washed in 70% ethanol and finally dried down.

Dideoxy sequencing

The protocol used was essentially as has been described (Biggin, M. D., Gibson, T. J., Hong, G.F.P.N.A.S. 80 3963–3965 (1983)).

We claim:

1. An insulin-like Growth Factor II (IGF-II) analogue in which at least one of R37 and R38, wherein R37 represents the natural arginine residue at position 37 and R38 represents the natural arginine residue at position 38 of SEQ. ID NO. 1, is replaced with another amino acid resid